(12) United States Patent
Burckhardt

(10) Patent No.: US 7,906,673 B2
(45) Date of Patent: Mar. 15, 2011

(54) ALDIMINOALKYLSILANES

(75) Inventor: Urs Burckhardt, Zürich (CH)

(73) Assignee: Sika Technology AG, Baar (CH)

( * ) Notice: Subject to any disclaimer, the term of this patent is extended or adjusted under 35 U.S.C. 154(b) by 734 days.

(21) Appl. No.: 10/582,867

(22) PCT Filed: Dec. 17, 2004

(86) PCT No.: PCT/EP2004/053589
§ 371 (c)(1), (2), (4) Date: Oct. 29, 2007

(87) PCT Pub. No.: WO2005/058921
PCT Pub. Date: Jun. 30, 2005

(65) Prior Publication Data
US 2008/0138522 A1    Jun. 12, 2008

(30) Foreign Application Priority Data
Dec. 18, 2003    (EP) .................................... 03029160

(51) Int. Cl.
*C07F 7/04*    (2006.01)
(52) U.S. Cl. ........................................ 556/465; 427/387
(58) Field of Classification Search ................ 427/387
See application file for complete search history.

(56) References Cited

U.S. PATENT DOCUMENTS

| 2,942,019 A | 6/1960 | Pike et al. |
| 3,681,420 A | 8/1972 | Brown et al. |
| 4,555,561 A | 11/1985 | Sugimori et al. |
| 4,853,454 A * | 8/1989 | Merger et al. .................. 528/59 |
| 5,010,161 A * | 4/1991 | Aoki et al. ...................... 528/59 |
| 5,134,234 A | 7/1992 | Parrinello et al. |

FOREIGN PATENT DOCUMENTS

| EP | 0 164 520 A1 | 12/1985 |
| EP | 0 985 693 A1 | 3/2000 |
| JP | A 10-147588 | 6/1998 |

* cited by examiner

*Primary Examiner* — Michael Barr
*Assistant Examiner* — Robert S Walters, Jr.
(74) *Attorney, Agent, or Firm* — Oliff & Berridge, PLC

(57) ABSTRACT

The invention relates to aldiminoalkylsilanes ALS which are preparable from the reaction of at least one aminoalkylsilane AS of the formula (I) and at least one aldehyde ALD of the formula (II), and to processes for preparing them. Additionally disclosed are the use of these aldiminoalkylsilanes in compositions comprising amine-reactive compounds, especially polyurethane compositions, and also in adhesion promoter compositions. The aldiminoalkylsilanes ALS and the compositions comprising them have the great advantage that they are low in odor or odorless and also stable on storage.

27 Claims, No Drawings

ALDIMINOALKYLSILANES

TECHNICAL FIELD

The invention relates to innovative aldiminoalkylsilanes, obtainable from the reaction of aminoalkylsilanes with specific aldehydes in a suitable way, which are suitable as adhesion promoters in polymer compositions, especially moisture-curing polyurethane compositions, and as part of adhesion promoter compositions. In the absence of moisture, the aldiminoalkylsilanes are stable on storage together with polyurethane compositions containing isocyanate groups, and when employed give rise to little or if any odor.

PRIOR ART

It is known that organoalkoxysilanes are suitable as adhesion promoters between polymer compositions such as polyurethane compositions, for example, and substrates such as glass, concrete or various metals, for example, described for example in "Silanes and Other Coupling Agents", K. L. Mittal (ed.), VSP 1992, page 21ff. They can be used, for example, as undercoats, as additives to primers, to pretreat fillers or as additives to adhesives, sealants and coatings, and are able to improve the adhesion of these compositions to a range of substrates.

Of particular interest as adhesion promoters are aminoalkylsilanes. Their amino group is able to enter into a chemical bond with polymer compositions such as polyurethane compositions, for example, by reaction with an isocyanate group, for example. In order to improve the adhesion of polymer compositions to substrates such as glass, for example, it is common to use aminoalkylsilanes, which are typically applied in diluted form, as an undercoat or as a primer, to the substrate before the polyurethane composition is applied thereto. In order to save this additional workstep of substrate pretreatment it would be desirable to incorporate aminoalkylsilane adhesion promoters directly into the polymer composition. In the case of moisture-curing polyurethane compositions, which contain free isocyanate groups, however, this is a problem, since the aminoalkylsilanes react directly with the isocyanate groups, thereby very largely losing their adhesion promoter effect and leading to inadequate storage stability of the compositions. In order to be able to utilize the good properties of aminoalkylsilanes as adhesion promoters in moisture-curing polyurethane compositions, therefore, it would be advantageous to incorporate the aminoalkylsilanes into the composition in a form initially not reactive toward isocyanate groups.

It is known that amines can be brought into a form which is not reactive toward isocyanate groups by converting them into aldimines. On contact with water, they undergo hydrolysis to form amines again, with liberation of aldehydes.

U.S. Pat. No. 2,942,019 and U.S. Pat. No. 3,681,420 describe iminoalkylsilanes prepared from aminoalkylsilanes and aldehydes (leading to aldiminoalkylsilanes) or ketones (leading to ketiminoalkylsilanes). EP 0 164 520 discloses polyurethane preparations which contain isocyanate groups and comprise an adhesion promoter in the form of organoalkoxysilanes containing aldimino or ketimino groups.

These known prior art iminoalkylsilanes feature two difficulties. On the one hand their storage stability together with moisture-curing polyurethane compositions, especially those which contain reactive aromatic isocyanate groups, is inadequate; that is, the viscosity of the polyurethane composition rises during storage, significantly, as a result of the presence of the iminoalkylsilane. On the other hand, many of the stated iminoalkylsilanes liberate, on hydrolysis, aldehydes or ketones which have an intense, disruptive odor, which for those having close contact with such substances is unpleasant and may trigger headaches, nausea or other health difficulties. Consequently, odor-intensive aldehydes or ketones, or the iminoalkylsilanes derived from them, can be employed only to a limited extent, since it is necessary always to ensure effective ventilation or to wear respiratory protection. They are therefore not suitable as adhesion promoters in compositions which are intended to cure as far as possible without developing odor, examples being those compositions which are employed in the interior of enclosed spaces.

U.S. Pat. No. 5,134,234 likewise describes iminoalkylsilanes. They are prepared in a complicated multistage process which starts from expensive and toxicologically objectionable isocyanatoalkylsilanes that are difficult to obtain.

EP 0 985 693 mentions iminoalkylsilanes which are stable on storage together with specific aliphatic isocyanates which contain isocyanate groups attached to a tertiary or secondary carbon atom and as a result have a low reactivity. Together with the much more reactive aromatic isocyanate groups, however, the majority of the iminoalkylsilanes mentioned are not stable on storage. On hydrolysis, the iminoalkylsilanes mentioned liberate odor-intensive aldehydes or ketones and for numerous applications they are therefore unsuitable. Furthermore, in the preparation of the iminoalkylsilanes as described in the patent text, the water produced is not removed, leading automatically to a high proportion of condensation products in the form of organosiloxanes. In order to be effective adhesion promoters, however, experience suggests that the aldiminoalkylsilanes ought not to have too great a degree of precondensation.

Aldiminoalkylsilanes which are preparable in good quality in a simple process, are stable on storage in the absence of moisture together with polyurethane compositions containing isocyanate groups, including in particular those containing reactive aromatic isocyanate groups, and which on hydrolysis give rise to very little odor, if any, have been hitherto unknown.

DESCRIPTION OF THE INVENTION

It is an object of the present invention to provide innovative aldimino-alkylsilanes which are preparable in good quality in a simple process, are stable on storage in the absence of moisture together with polyurethane compositions containing isocyanate groups, including in particular those containing reactive aromatic isocyanate groups, and which on hydrolysis give rise to very little odor, if any. Aldiminoalkylsilaness of this kind are able to improve the adhesion of polymer compositions on a range of substrates. They are suitable, for example, as an addition to moisture-curing polyurethane compositions or as a constituent of adhesion promoter compositions.

It has been found that aldiminoalkylsilanes which meet the stated conditions are obtainable simply and in good quality through the reaction of at least one aminoalkylsilane with at least one specific aliphatic aldehyde having, in a position a to the aldehyde carbonyl group, a tertiary carbon atom, i.e., a carbon atom which does not possess a bond to a hydrogen atom. aldiminoalkylsilaness of good quality are those present only to a small extent in condensed form (as organosiloxanes). The reason for the difficulty of preparing aldiminoalkylsilanes in good quality is that the formation of the aldimino group from an amino and an aldehyde group is accompanied by release of one mole of water per mole of amino group. This is a problem insofar as the silane groups present can be unwantedly hydrolyzed by the water formed, and can form condensation products in the form of organosiloxanes. If this occurs, aldiminoalkylsilanes of poor quality are obtained, which have no adhesion promoter effect, or only an unsatisfactory adhesion promoter effect, which are of high viscosity, or which include inhomogeneous fractions in the form of suspended condensation products.

It has been found that aldiminoalkylsilanes of excellent quality are obtained if the water formed in the reaction of the aminoalkylsilane with the aldehyde is removed appropriately from the reaction mixture before it can hydrolyze the silane group.

The aldiminoalkylsilanes of the invention are stable on storage together with moisture-curing polyurethane compositions for several weeks and months. This is the case in particular even when the polyurethane compositions contain reactive aromatic isocyanate groups, as are present, for example, in diphenylmethane 4,4'-diisocyanate (MDI) or tolylene 2,4- and 2,6-diisocyanate (TDI). In contrast to this, the majority of prior art iminoalkylsilanes, together with polyurethane compositions containing isocyanate groups, especially those containing reactive aromatic isocyanate groups, are stable on storage for only a short time, or not at all, and in the course of storage lead to a marked to sharp increase in the viscosity of the polyurethane composition.

A further important aspect of the aldiminoalkylsilanes of the invention is the fact that, before, during, and after their use, they cause little if any odor. This is achieved by virtue of the fact that the aldehyde used for preparing the aldiminoalkylsilanes, which is liberated again by hydrolysis when the aldiminoalkylsilanes are used, is low in odor or odorless. Accordingly, the aldiminoalkylsilanes of the invention are suitable as an addition to polymer compositions, especially moisture-curing polyurethane compositions, which, before, during, and after their curing, are intended to produce little if any odor, as required, for example, for seals, adhesive bonds or coatings in enclosed spaces, such as in the interior of vehicles or buildings, for example. They are additionally suitable as a constituent of adhesion promoter compositions, especially those with a long open time.

WAYS OF PERFORMING THE INVENTION

The present invention relates to aldiminoalkylsilanes ALS which are obtainable from at least one aminoalkylsilane AS of formula (I) and at least one aldehyde ALD of formula (II).

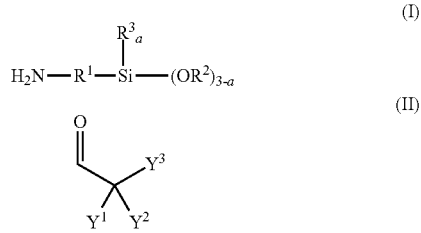

$R^1$ in this case is a linear or branched, optionally cyclic, alkylene group having 1 to 20 carbon atoms, optionally with aromatic components, and optionally with one or more heteroatoms, especially nitrogen atoms.

$R^2$ is an alkyl group having 1 to 5 carbon atoms, preferably is a methyl group or is an ethyl group or is an isopropyl group, in particular is a methyl group or is an ethyl group.

$R^3$ is an alkyl group having 1 to 8 carbon atoms, preferably is a methyl group or is an ethyl group, in particular is a methyl group.

$a$ is 0, 1 or 2.

$Y^1$ and $Y^2$ either independently of one another are each an organic radical; or together they form a carbocyclic or heterocyclic ring which has a size of between 5 and 8, preferably 6, atoms.

$Y^3$ either is a substituted or unsubstituted alkyl group which has at least one heteroatom;

or is a branched or unbranched alkyl or alkylene group having at least 10 carbon atoms;

or is a substituted or unsubstituted aryl or arylalkyl group;

or is O—$R^4$ or

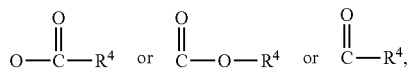

where $R^4$ in turn is an alkyl, arylalkyl or aryl group having at least 3 carbon atoms and is in each case substituted or unsubstituted.

The prefix "poly" in substance names such as "polyol", "polyisocyanate", "polyamine" or "polyaldimine" refers in the present document to the fact that the substance in question formally contains per molecule more than one of the functional groups which occurs in its name.

The term "polymer" refers in the present document on the one hand to a group of chemically uniform macromolecules which nevertheless differ in respect of degree of polymerization, molar mass, and chain length and have been prepared by a polymerization reaction (addition polymerization, polyaddition, polycondensation). On the other hand the term "polymer" in this document also embraces derivatives of such a group of macromolecules from polymerization reactions, in other words compounds which have been obtained by reactions, such as addition reactions or substitution reactions, for example, of functional groups on existing macromolecules and which may be chemically uniform or chemically nonuniform.

The term "polymer composition" refers in the present document to a homogeneous or heterogeneous mixture of substances which is composed of one or more polymers or comprises polymers to a substantial extent.

The term "polyurethane" embraces, in the present document, all polymers prepared by the diisocyanate polyaddition process. This includes those polymers which are virtually or entirely free from urethane groups, such as polyether-polyurethanes, polyester-polyurethanes, polyether-polyureas, polyureas, polyester-polyureas, polyisocyanurates, polycarbodiimides, etc.

By "organoalkoxysilanes" or "silanes" for short are meant, in the present document, specific organosilicon compounds in which on the one hand there are at least one, typically two or three, alkoxy group(s) attached directly to the silicon atom (via an Si—O bond) and which on the other hand have at least one organic radical attached directly to the silicon atom (via an Si—C bond). Corresponding to this, the term "silane group" in the present document refers to the silicon-containing group attached to the organic radical of the organoalkoxysilane. The organoalkoxysilanes, and their silane groups, have the property of hydrolyzing on contact with moisture. This forms organosilanols, in other words organosilicon compounds containing one or more silanol groups (Si—OH groups) and, as a result of subsequent condensation reactions, organosiloxanes, in other words organosilicon compounds containing one or more siloxane groups (Si—O—Si groups).

By "aminoalkylsilanes" are meant, in the present document, specific organoalkoxysilanes whose organic radical attached directly to the silicon atom carries at least one primary amino group ($NH_2$ group).

By "aldiminoalkylsilanes" are meant, in the present document, specific organoalkoxysilanes whose organic radical attached directly to the silicon atom carries at least one aldimino group (CH=N group).

Aldiminoalkylsilanes ALS are preparable from at least one aminoalkylsilane AS of formula (I) and from at least one aldehyde ALD of formula (II) by means of a condensation reaction with liberation of water. Condensation reactions between amines and aldehydes are very well known and are described in Houben-Weyl, "Methoden der organischen Chemie", Vol. XI/2, page 73 ff, for example. In the present case the amine used is an aminoalkylsilane. This includes the additional difficulty that the water liberated during the condensation can lead to hydrolysis of the silane groups. That reaction, however, is unwanted and must be substantially suppressed in order for a good-quality product to be obtained. Otherwise, with renewed liberation of water, condensation products are formed in the form of organosiloxanes, i.e., in the present case, molecules which are composed of two or more aldiminoalkylsilanes connected via siloxane groups. This is a problem insofar as these condensation products are of only limited availability, or none at all, for the development of adhesion on a substrate, and, consequently, poor-quality aldiminoalkylsilanes of this kind substantially lose their desired effect as adhesion promoters. For the preparation of a good-quality aldiminoalkylsilane ALS it is critical to select a preparation method in which the hydrolysis of the silane groups is very extensively suppressed.

For the preparation of an aldiminoalkylsilane ALS a method is preferred in which the aminoalkylsilane AS is introduced initially and the aldehyde ALD is added dropwise. It is critical to remove the water formed during the reaction from the reaction mixture, by, for example, permanently applying vacuum to strip off the water liberated during the condensation immediately, or by removing said water using a water absorber, such as a suitable molecular sieve, for example. The reaction can be carried out at temperatures from 5° C. to 250° C. A preferred reaction temperature, however, is in the range of 20-100° C.

It is likewise possible to prepare an aldiminoalkylsilane ALS by initially introducing the aldehyde ALD and adding the aminoalkylsilane AS dropwise. In this way, experience has shown that aldiminoalkylsilanes of low quality are produced, which often exhibit a precipitate, caused by the disproportionately substantial formation of condensation products.

Typically such reactions are carried out in the presence of a solvent which forms an azeotrope with water, the water being removed together with the solvent from the reaction mixture. It is preferred, however, to prepare the aldiminoalkylsilane ALS using the alcohol which is liberated during the hydrolysis of the silane groups—methanol when using a methoxysilane, or ethanol when using an ethoxysilane. It has been observed that, when the aminoalkylsilane AS is introduced as an initial charge in the corresponding alcohol, and the aldehyde ALD is added dropwise with immediate removal of the water, aldiminoalkylsilanes ALS of outstanding quality are obtained. It is, however, also possible to obtain good-quality aldiminoalkylsilanes ALS by doing entirely without the use of solvents in the course of their preparation. In that case the aminoalkylsilane AS is introduced initially and the aldehyde ALD is added dropwise under reduced pressure.

In a further preferred form of preparation, aldiminoalkylsilanes ALS are prepared in or together with polyaldimines. In this case either first a polyaldimine is prepared by reacting a polyamine with an aldehyde, in particular an aldehyde ALD of the formula (II), with removal of water, and subsequently, in this polyaldimine, an aldiminoalkylsilane ALS is prepared by reacting an aminoalkylsilane AS with an aldehyde ALD with removal of water. Alternatively, the preparation of the aldiminoalkylsilane ALS and of the polyaldimine takes place simultaneously, by reacting a mixture of an aminoalkylsilane AS and of a polyamine with an aldehyde ALD with removal of water. These reactions are preferably carried out without using solvents. The solutions obtained in this way, solutions of aldiminoalkylsilanes ALS in polyaldimines, are distinguished by very low condensation product contents and by low viscosities. Polyaldimines here are prepared from at least one polyamine having primary aliphatic amino groups and at least one aldehyde by means of a condensation reaction, with liberation of water, by means of known processes, described for example in Houben-Weyl, "Methoden der organischen Chemie", Vol. XI/2, page 73 ff.

For the preparation of the aldiminoalkylsilane ALS the aldehyde groups of the aldehyde ALD are employed stoichiometrically or in a stoichiometric excess in relation to the primary amino groups of the aminoalkylsilane AS.

In the preparation of an aldiminoalkylsilane ALS it is possible if desired to use catalysts, examples being acids such as alkylbenzenesulfonic acids, alkylsulfonic acids, trifluoroacetic acid, acidic phosphoric esters, mineral acids, boron trifluoride complexes or aluminum chloride complexes, for example.

It is further possible to purify the aldiminoalkylsilanes ALS after they have been prepared, in an additional workstep, by distillation for example, and so to separate them completely from any condensation products present.

Suitable aminoalkylsilanes AS for preparing an aldiminoalkylsilane ALS are compounds of the formula (I).

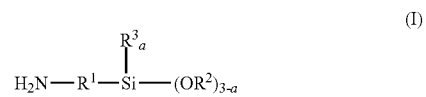

(I)

$R^1$ in this case is a linear or branched, optionally cyclic, alkylene group having 1 to 20 carbon atoms, optionally with aromatic components, and optionally with one or more heteroatoms, especially nitrogen atoms.

$R^2$ is an alkyl group having 1 to 5 carbon atoms, preferably is a methyl group or is an ethyl group or is an isopropyl group, in particular is a methyl group or is an ethyl group.

$R^3$ is an alkyl group having 1 to 8 carbon atoms, preferably is a methyl group or is an ethyl group, in particular is a methyl group.

a is 0, 1 or 2.

$R^1$ is preferably a methylene, propylene, methylpropylene, butylene or dimethylbutylene group, in particular a propylene group.

Examples that may be mentioned of suitable aminoalkylsilanes AS of the formula (I) include the following:

3-aminopropyltrimethoxysilane, 3-aminopropyldimethoxymethylsilane, 3-amino-2-methylpropyltrimethoxysilane, 4-aminobutyltrimethoxysilane, 4-aminobutyldimethoxymethylsilane, 4-amino-3-methylbutyltrimethoxysilane, 4-amino-3,3- dimethylbutyltrimethoxysilane, 4-amino-3,3-dimethylbutyldimeth-oxymethylsilane, 2-aminoethyltrimethoxysilane, 2-aminoethyldimethoxymethylsilane, aminomethyltrimethoxysilane, aminomethyldimethoxymethylsilane, aminomethylmethoxydimethylsilane, N-(2-aminoethyl)-3-aminopropyltrimethoxysilane, N-(2-aminoethyl)-3-aminopropyldimethoxymethylsilane, 7-amino-4-oxaheptyidimethoxymethylsilane, and also their analogs with ethoxy or isopropoxy groups instead of the methoxy groups.

Preferred aminoalkylsilanes AS of the formula (I) are 3-aminopropyl-trimethoxysilane, 3-aminopropyltriethoxysilane, 4-amino-3,3-dimethylbutyl-trimethoxysilane, N-(2-aminoethyl)-3-aminopropyltrimethoxysilane or N-(2-aminoethyl)-3-aminopropyltriethoxysilane, especially 3-aminopropyltrimethoxy-silane and 3-aminopropyltriethoxysilane.

Where aldiminoalkylsilanes ALS are to be prepared in a mixture with polyaldimines, suitability for preparing the polyaldimines is possessed by commercially customary polyamines having primary aliphatic amino groups, of the kind which, among other things, are used for two-component polyurethanes. Polyamines of this kind contain formally per molecule two or more primary amino groups ($NH_2$ groups) attached to an aliphatic, cycloaliphatic or arylaliphatic radical. Examples that may be mentioned include the following polyamines: ethylenediamine, 1,2- and 1,3-propanediamine, 2-methyl-1,2-propanediamine, 2,2-dimethyl-1,3-propanediamine, 1,3- and 1,4-butanediamine, 1,3- and 1,5-pentanediamine, 1,6-hexamethylenediamine, 2,2,4- and 2,4,4-trimethylhexamethylenediamine and mixtures thereof, 1,7-heptanediamine, 1,8-octanediamine, 4-aminomethyl-1,8-octanediamine, 1,9-nonanediamine, 1,10-decanediamine, 1,11-undecanediamine, 1,12-dodecanediamine, methylbis(3-aminopropyl)amine, 1,5-diamino-2-methyl-pentane (MPMD), 1,3-diaminopentane (DAMP), 2,5-dimethyl-1,6-hexa-methylenediamine, cycloaliphatic polyamines such as 1,2-, 1,3- and 1,4-diaminocyclohexane, bis(4-aminocyclohexyl)methane, bis(4-amino-3-methylcyclohexyl)methane, bis(4-amino-3-ethylcyclohexyl)methane, bis(4-amino-3,5-dimethylcyclohexyl)methane, 1-amino-3-aminomethyl-3,5,5-tri-methylcyclohexane (isophoronediamine or IPDA), 2- and 4-methyl-1,3-diamino-cyclohexane and mixtures thereof, 1,3- and 1,4-bis(aminomethyl)cyclohexane, 1-cyclohexylamino-3-aminopropane, 2,5(2,6)-bis(aminomethyl)bicyclo[2.2.1]-heptane (NBDA, produced by Mitsui Chemicals), 3(4),8(9)-bis(aminomethyl)-tricyclo[5.2.1.0$^{2,6}$]decane, 1,4-diamino-2,2,6-trimethylcyclohexane (TMCDA), 3,9-bis(3-aminopropyl)-2,4,8,10-tetraoxaspiro[5.5]undecane, 1,3- and 1,4-xylylenediamine, aliphatic polyamines containing ether groups, such as bis(2-aminoethyl)ether, 4,7-dioxadecane-1,10-diamine, 4,9-dioxadodecane-1,12-diamine and higher oligomers thereof, polyoxyalkylene-polyamines having theoretically two or three amino groups, available for example under the name Jeffaminee (produced by Huntsman Chemicals), and mixtures of the aforementioned polyamines.

Preferred polyamines are 1,6-hexamethylenediamine, MPMD, DAMP, 2,2,4- and 2,4,4-trimethylhexamethylenediamine, 4-aminomethyl-1,8-octane-diamine, IPDA, 1,3- and 1,4-xylylenediamine, 1,3- and 1,4-bis(aminomethyl)-cyclohexane, bis(4-aminocyclohexyl)methane, bis(4-amino-3-methylcyclo-hexyl)methane, 3(4),8(9)-bis(aminomethyl)tricyclo[5.2.1.0$^{2,6}$]decane, 1,2-, 1,3- and 1,4-diaminocyclohexane, 1,4-diamino-2,2,6-trimethylcyclohexane, polyoxy-alkylene-polyamines having theoretically two or three amino groups, especially Jeffamine® EDR-148, Jeffamine® D-230, Jeffamine® D-400, and Jeffamine® T-403, and also, in particular, mixtures of two or more of the aforementioned polyamines.

To prepare an aldiminoalkylsilane ALS starting from an aminoalkylsilane AS an aldehyde ALD of the following formula (II) is used.

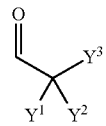

(II)

$Y^1$ and $Y^2$ either independently of one another are an organic radical; or together they form a carbocyclic or heterocyclic ring which has a size of between 5 and 8, preferably 6, atoms. Preferably $Y^1$ and $Y^2$ are identical and are in particular a methyl group.

$Y^3$ can be a substituted or unsubstituted alkyl group which has at least one heteroatom, particularly in the form of an ether oxygen, a carboxyl group or an ester group.

$Y^3$ can alternatively be a branched or unbranched alkyl or alkylene group having at least 10 carbon atoms.

In addition $Y^3$ may also be a substituted or unsubstituted aryl or arylalkyl group.

Finally $Y^3$ can also be a radical of the formula for O—$R^4$ or

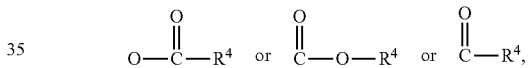

where $R^4$ in turn is an alkyl, arylalkyl or aryl group having at least 3 carbon atoms and is in each case substituted or unsubstituted.

The aldehydes ALD of the formula (II) have the quality of being either low in odor or odorless, and of therefore causing only little, if any, development of odor.

By a substance "low in odor" and a substance which "causes little development of odor" is meant, without distinction, a substance whose odor is acceptable to human beings only to a small extent, i.e., which can be smelt only to a small extent, and which, therefore, does not have intense odor, such as, for example, formaldehyde, acetaldehyde, isobutyraldehyde, pivalaldehyde or solvents such as acetone, methyl ethyl ketone or methyl isobutyl ketone, this low odor being perceived by the majority of human beings to be not unpleasant or repellent.

An "odorless" substance is a substance which the majority of human beings are unable to smell, and which therefore has no perceptible odor.

Examples of compounds of formula (II) are:

ethers of 2-hydroxy-2-methylpropanal and alcohols such as propanol, isopropanol, butanol, and 2-ethylhexanol; esters of 2-formyl-2-methylpropionic acid and alcohols such as propanol, isopropanol, butanol, and 2-ethylhexanol; esters of 2-hydroxy-2-methylpropanal and carboxylic acids such as butyric acid, isobutyric acid, and 2-ethylhexanoic acid; and also the aldehydes listed below as being particularly suitable.

Particularly suitable compounds are, on the one hand, those of formula (III)

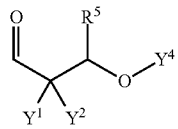

(III)

where $R^5$ is a hydrogen atom or is an alkyl or arylalkyl or aryl group and $Y^4$ is an alkyl, arylalkyl or aryl group, and $Y^1$ and $Y^2$ have the definition already described.

Examples that may be mentioned of compounds of the formula (III) are ethers of β-hydroxyaldehydes, as formed from a crossed aldol reaction from formaldehyde and a second aldehyde such as 2-methylbutyraldehyde, 2-ethyl-butyraldehyde, 2-methylvaleraldehyde, 2-ethylcaproaldehyde, cyclopentane-carboxaldehyde, cyclohexanecarboxaldehyde, 1,2,3,6-tetrahydrobenz-aldehyde, 2-methyl-3-phenylpropionaldehyde, 2-phenylpropionaldehyde (hydratropaldehyde), and diphenylacetaldehyde, and alcohols such as methanol, ethanol, propanol, isopropanol, butanol, 2-ethylhexanol or fatty alcohols, such as, for example, 3-methoxy- and 3-ethoxy- and 3-propoxy- and 3-isopropoxy- and 3-butoxy-, and also 3-(2-ethylhexoxy)-2,2-dimethylpropanal.

Particularly suitable on the other hand are compounds of formula (IV),

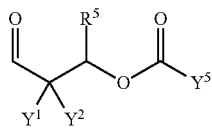

(IV)

where $Y^1$, $Y^2$ and $R^5$ have the definition already described, and $Y^5$ either is a hydrogen atom;

or is an alkyl or arylalkyl or aryl group which optionally has at least one heteroatom, in particular an ether oxygen, optionally contains at least one carboxyl group and optionally contains at least one ester group;

or is a mono- or polyunsaturated, linear or branched hydrocarbon chain.

Examples of preferred aldehydes of the formula (IV) are products of an esterification of the aforementioned β-hydroxyaldehydes such as 3-hydroxy-pivalaldehyde, 3-hydroxyisobutyraldehyde, 3-hydroxypropionaldehyde, 3-hydroxybutyraldehyde, 3-hydroxyvaleraldehyde, 2-hydroxymethyl-2-methyl-butyraldehyde, 2-hydroxymethyl-2-ethylbutyraldehyde, 2-hydroxymethyl-2-methylvaleraldehyde, 2-hydroxymethyl-2-ethylhexanal, 1-hydroxymethyl-cyclopentanecarbaldehyde, 1-hydroxymethylcyclohexanecarbaldehyde, 1-hydroxymethylcyclohex-3-enecarbaldehyde, 2-hydroxymethyl-2-methyl-3-phenylpropionaldehyde, 3-hydroxy-2-methyl-2-phenylpropionaldehyde and 3-hydroxy-2,2-diphenylpropionaldehyde with carboxylic acids such as formic acid, acetic acid, propionic acid, butyric acid, isobutyric acid, 2-ethylcaproic acid, and benzoic acid, and also the aldehydes listed below as being particularly preferred.

In one particularly preferred embodiment use is made of aldehydes ALD of the formula (IV) which are odorless and whose radicals $R^5$ and $Y^5$ are restricted as follows:

$R^5$ is a hydrogen atom, and $Y^5$ is alternatively a linear or branched alkyl chain having 11 to 30 carbon atoms, optionally having at least one heteroatom, in particular having at least one ether oxygen;

or is a mono- or polyunsaturated, linear or branched hydrocarbon chain having 11 to 30 carbon atoms;

or is a radical of the formula (V) or (VI).

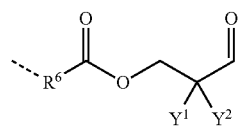

(V)

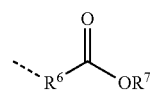

(VI)

In the formulae (V) and (VI) $R^6$ is a linear or branched or cyclic alkylene chain having 2 to 16 carbon atoms, optionally having at least one heteroatom, in particular having at least one ether oxygen, or is a mono- or polyunsaturated, linear or branched or cyclic hydrocarbon chain having 2 to 16 carbon atoms, and $R^7$ is a linear or branched alkyl chain having 1 to 8 carbon atoms, and $Y^1$ and $Y^2$ have the definition already described.

The dashed line in the formulae (V) and (VI) identifies the bonding site in each case.

The embodiment of the invention just described makes it possible to prepare not only aldiminoalkylsilanes ALS with a low development of odor but also those entirely without acceptable odor. This is particularly advantageous for applications in the interior of buildings and vehicles.

Examples of the particularly preferred odorless aldehydes ALD of the formula (IV) which lead to odorless aldiminoalkylsilanes ALS are esterification products of the aforementioned β-hydroxyaldehydes such as 3-hydroxy-pivalaldehyde, 3-hydroxyisobutyraldehyde, 3-hydroxypropanal, 3-hydroxy-butyraldehyde, 3-hydroxyvaleraldehyde, 2-hydroxymethyl-2-methyl-butyraldehyde, 2-hydroxymethyl-2-ethylbutyraldehyde, 2-hydroxymethyl-2-methylvaleraldehyde, 2-hydroxymethyl-2-ethylhexanal, 1-hydroxymethyl-cyclopentanecarbaldehyde, 1-hydroxymethylcyclohexanecarbaldehyde, 1-hydroxymethylcyclohex-3-enecarbaldehyde, 2-hydroxymethyl-2-methyl-3-phenylpropionaldehyde, 3-hydroxy-2-methyl-2-phenylpropionaldehyde, and 3-hydroxy-2,2-diphenylpropionaldehyde with carboxylic acids such as, for example, lauric acid, tridecanoic acid, myristic acid, pentadecanoic acid, palmitic acid, margaric acid, stearic acid, nonadecanoic acid, arachidic acid, palmitoleic acid, oleic acid, erucic acid, linoleic acid, linolenic acid, eleostearic acid, arachidonic acid, succinic acid, glutaric acid, adipic acid, pimelic acid, suberic acid, azelaic acid, sebacic acid, 1,12-dodecanedioic acid, maleic acid, fumaric acid, hexahydrophthalic acid, hexahydroisophthalic acid, hexahydro-terephthalic acid, 3,6,9-trioxaundecanedioic acid, and similar derivatives of polyethylene glycol, dehydrogenated ricinoleic acids, and also fatty acids from the industrial saponification of natural oils and fats such as, for example, rapeseed oil, sunflower oil, linseed oil, olive oil, coconut oil, oil-palm kernel oil, and oil-palm oil.

Preferred carboxylic acids are lauric acid, myristic acid, palmitic acid, stearic acid, oleic acid, linoleic acid, linolenic acid, succinic acid, adipic acid, azelaic acid and sebacic acid, and technical mixtures of fatty acids that comprise these acids.

In one preferred preparation method of an aldehyde ALD of the formula (IV) a β-hydroxyaldehyde, such as one of the β-hydroxyaldehydes already mentioned, such as 3-hydroxypivalaldehyde, which can be prepared, for example, from formaldehyde (or paraformaldehyde or 1,3,5-trioxane) and isobutyraldehyde, in situ if desired, is reacted with a carboxylic acid, in particular a long-chain fatty acid, to give the corresponding ester, specifically either with a carboxylic acid $Y^5$—COOH to give the corresponding carboxylic ester of, for example, 3-hydroxypivalaldehyde; and/or with a dicarboxylic acid monoalkyl ester HOOC—$R^6$—$COOR^7$ to give the aldehyde of the formula (IV) with the radical $Y^5$ of formula (VI); and/or with a dicarboxylic acid HOOCR—$R^6$—COOH to give the aldehyde of the formula (IV), in this case a dialdehyde, with the radical $Y^5$ of formula (V). The formulae (V) and (VI), and $Y^5$, $R^6$, and $R^7$, here have the definition already described. This esterification can take place without the use of solvents, by known methods, described for example in Houben-Weyl, "Methoden der organischen Chemie", Vol. VII, pages 516-528.

Suitable carboxylic acids for esterification with a β-hydroxyaldehyde, such as with 3-hydroxypivalaldehyde, are, for example, the short-chain and long-chain carboxylic acids already specified.

The reaction of at least one aminoalkylsilane AS of formula (I) with at least one aldehyde ALD of formula (II) produces, for example, aldiminoalkylsilanes ALS of the formula (VII).

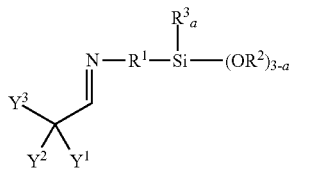
(VII)

As an aldehyde ALD for preparing an aldiminoalkylsilane ALS it is also possible to use a dialdehyde. A dialdehyde may, if desired, be reacted twice with an aminoalkylsilane AS, so that all of the aldehyde groups are condensed to aldimino groups. It is also possible, however, to use an excess of aldehyde groups in relation to the amino groups, so that some of the aldehyde groups are not reacted. If, for example, an aldehyde ALD of formula (IV) with $Y^5$ of formula (V) is used to prepare an aldiminoalkylsilane ALS and is reacted completely, i.e., twice, with an aminoalkylsilane AS, this produces compounds as depicted in formula (VIII).

It is also possible to use mixtures of different aminoalkylsilanes AS and/or different aldehydes ALD to prepare an aldiminoalkylsilane ALS.

The aldiminoalkylsilane ALS may include certain fractions of condensation products in the form of organosiloxanes. Even when employing optimized preparation methods which substantially suppress the formation of such condensation products, the resulting aldiminoalkylsilanes ALS nevertheless always include a fraction, albeit small, of condensation products, although this does not jeopardize their adhesion promoter effect. As already mentioned, the aldiminoalkylsilane ALS can be purified if desired, by means for example of distillation, in order to remove any condensation products there may be.

In the absence of moisture, the aldiminoalkylsilanes ALS are stable on storage, either alone or else in combination with amine-reactive components, such as isocyanates, for example. On contact with water there is hydrolysis not only of the aldimino groups but also of the silane groups. Water in this case can be brought into contact in the liquid or gaseous aggregate state, or in bound form, with the aldiminoalkylsilane ALS. Thus in a hydrolysis process, for example, it is possible for water in the form of atmospheric moisture to act on the aldiminoalkylsilane ALS or on a composition comprising the aldiminoalkylsilane ALS. Another example of a hydrolysis process is the mixing of water or a water-containing component or water-releasing component into a composition comprising aldiminoalkylsilane ALS. The water is brought into contact with aldiminoalkylsilane ALS preferably in the gaseous aggregate state, more preferably in the form of atmospheric moisture.

In the course of the hydrolysis the aldimino groups of the aldiminoalkylsilane ALS undergo a formal reaction to amino groups, with liberation of the corresponding aldehyde ALD. In the presence of amine-reactive groups such as isocyanate groups, for example, the amino groups undergo further reaction, to form, for example, urea groups. As a result the hydrolysis of the aldimino groups is rapid and complete. The liberated aldehyde ALD is odorless or low in odor. In other words it causes little development of odor, or none at all, in a composition such as, for example, an adhesive, sealant or covering.

The reaction of amine-reactive components with the hydrolyzing aldiminoalkylsilane ALS need not necessarily take place via the aminoalkylsilane. It will be appreciated that reactions with intermediate stages of hydrolysis of the aldiminoalkylsilane to the aminoalkylsilane are also possible. By way of example it is conceivable for the hydrolyzing aldiminoalkylsilane to react in the form of a hemiaminal directly with the amine-reactive components.

The silane groups of the aldiminoalkylsilane ALS react in the course of the hydrolysis to form organosilanols and, through subsequent condensation reactions, to form organosiloxanes. The aldiminoalkylsilanes possess the capacity to develop strong adhesion to a variety of substrates and/or to enhance the development of adhesion of a polymer compo-

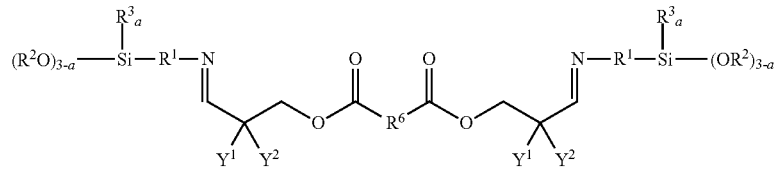
(VIII)

sition to a substrate. The development of adhesion possibly involves primarily the silanol groups, which, instead of exclusively undergoing condensation with one another to form organosiloxanes, enter partly into a bond with the respective substrate.

In order to accelerate the hydrolysis not only of the aldimino groups but also of the silane groups, it can be advantageous to combine the aldiminoalkylsilane ALS with appropriate catalysts.

Examples of catalysts appropriate for the hydrolysis of the aldimino groups include organic carboxylic acids such as benzoic acid or salicylic acid, an organic carboxylic anhydride such as phthalic anhydride or hexahydrophthalic anhydride, a silyl ester of organic carboxylic acids, an organic sulfonic acid such as p-toluenesulfonic acid or 4-dodecylbenzenesulfonic acid, or another organic or inorganic acid, or mixtures of the aforementioned acids.

Examples of catalysts appropriate for the hydrolysis of the silane groups include organotin compounds such as dibutyltin dilaurate, dibutyltin diacetylacetonate, organobismuth compounds or bismuth complexes, or compounds containing amino groups, such as 1,4-diazabicyclo[2.2.2]octane or 2,2'-dimorpholinodiethyl ether, for example.

The aldiminoalkylsilanes ALS are suitable, for example, as adhesion promoters for polymer compositions such as adhesives, sealants or coatings on a variety of substrates, for example. In this context they can be employed either as a constituent of the polymer compositions, in particular of moisture-curing polymer compositions, preferably polymer compositions containing isocyanate groups and/or silane groups, more preferably moisture-curing polyurethane compositions. Or they can be used as a constituent of an adhesion promoter composition in the form, for example, of a cleaning product, an adhesion promoter solution, a pretreatment agent or a primer, in order to improve the adhesion of a polymer composition to the substrate pretreated with the adhesion promoter composition.

Examples of suitable substrates for the application of aldiminoalkylsilanes ALS as adhesion promoters include inorganic substrates such as, for example, glass, glass ceramic, concrete, mortar, brick, tile, plaster and natural stone such as granite or marble; metals such as aluminum, steel, nonferrous metals, galvanized metals; organic substrates such as wood, plastics such as PVC, polycarbonates, PMMA, polyesters, epoxides; coated substrates such as, for example, powder-coated metals; and also paints and varnishes, especially automotive topcoats. Preferred substrates are glass, glass ceramic, concrete, natural stone, aluminum, and automotive topcoats.

The aldiminoalkylsilanes ALS are especially suitable as constituents of polymer compositions which contain amine-reactive components, such as, for example, polyurethane compositions containing isocyanate groups, especially compositions containing reactive aromatic isocyanate groups. Polyurethane compositions of this kind, indeed, as a mixture with aldiminoalkylsilanes ALS, are stable on storage for from several months up to a year without loss of their usefulness. Not stable on storage, in contrast, are isocyanate-containing polyurethane compositions, especially those containing reactive aromatic isocyanate groups and containing aminoalkylsilanes or the majority of iminoalkylsilanes of the prior art. Examples of silanes not stable on storage together with polyurethane compositions containing aromatic isocyanate groups are ketiminoalkylsilanes. Likewise not stable on storage in such compositions, experience has shown, are aldiminoalkylsilanes which are reaction products of aminoalkylsilanes and primary or secondary aliphatic aldehydes such as butyraldehyde or isobutyraldehyde—in other words, aldiminoalkylsilanes which in the position α to the carbon atom of the aldimino group have a CH or a $CH_2$ moiety. The same is true of aldiminoalkylsilanes which are reaction products of aromatic aldehydes such as, for example, benzaldehyde and aminoalkylsilanes whose primary amino group is attached to a primary carbon atom, such as, for example, 3-aminopropyltrimethoxysilane and also the majority of commercially customary aminoalkylsilanes.

The terms "stable on storage" and "storage stability" in connection with a polyurethane composition containing isocyanate groups and comprising an organoalkoxysilane is used in the present document in each case to refer to the situation where the viscosity of said composition during storage in the absence of moisture undergoes little or no increase over a period of several months up to a year or more, as a result of the presence of the organoalkoxysilane, and where the composition continues to be useful after storage.

The aldiminoalkylsilanes ALS have the capacity to be low in odor or odorless and also to liberate, when hydrolyzed, an aldehyde ALD which is low in odor or odorless. As a consequence of this they are highly suitable specifically for applications where the product must not constitute more than minimal odor nuisance, either before, during or after its use.

As already mentioned, the aldiminoalkylsilanes ALS described can be used, for example, as a constituent of moisture-curing polyurethane compositions. A polyurethane composition of this kind is composed of a polyurethane polymer, containing isocyanate groups, and, optionally, of further components.

A suitable polyurethane polymer for a polyurethane composition of this kind is prepared from at least one polyisocyanate and at least one polyol. The reaction can take place by reacting the polyol and the polyisocyanate by typical processes, for example at temperatures of 50° C. to 100° C., with the use if desired of appropriate catalysts, the polyisocyanate being used in an amount such that its isocyanate groups are present in a stoichiometric excess in relation to the hydroxyl groups of the polyol. The excess of polyisocyanate is selected such that the resulting polyurethane polymer, after all of the hydroxyl groups of the polyol have reacted, is left, for example, with a free isocyanate group content of 0.1 to 15% by weight, preferably 0.5 to 5% by weight, based on the polyurethane polymer as a whole. If desired, the polyurethane polymer can be prepared using plasticizers, in which case the plasticizers used contain no isocyanate-reactive groups.

Polyols which can be used for preparing such a polyurethane polymer may include, for example, the following, commercially customary polyols, or any desired mixtures of them:

Polyoxyalkylene polyols, also called polyether polyols, which are addition-polymerization products of ethylene oxide, 1,2-propylene oxide, 1,2- or 2,3-butylene oxide, tetrahydrofuran or mixtures thereof, optionally polymerized by means of a starter molecule having two or more active hydrogen atoms, such as water, for example, ammonia, or compounds having two or more OH or NH groups, such as 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline, and mixtures of the aforementioned compounds. Use may be made not only of polyoxyalkylene polyols which have a low degree of unsaturation (measured by ASTM D-2849-69 and expressed in milliequivalents of unsaturation per gram of polyol (meq/g)), prepared for example by means of what are called double metal cyanide complex catalysts (DMC catalysts), but also of polyoxyalkylene polyols having a higher degree of unsaturation, prepared for example using anionic catalysts such as NaOH, KOH or alkali metal alkoxides.

Particular suitability is possessed by polyoxyalkylene diols or polyoxy-alkylene triols, especially polyoxypropylene diols or polyoxypropylene triols.

Especially suitable polyoxyalkylene diols or polyoxyalkylene triols are those having a degree of unsaturation of less than 0.02 meq/g and having a molecular weight in the range from 1000 to 30 000 g/mol, and also polyoxy-propylene diols and triols having a molecular weight of 400 to 8000 g/mol. By "molecular weight" or "molar weight" is meant, in the present document, always the molecular weight average $M_n$.

Likewise particularly suitable are what are called "EO-endcapped" (ethylene oxide-endcapped) polyoxypropylene diols or triols. The latter are special polyoxypropylene-polyoxyethylene polyols which are obtained, for example, by subjecting pure polyoxypropylene polyols, after the end of the polypropoxylation, to alkoxylation with ethylene oxide, and which, as a result, have primary hydroxyl groups.

Hydroxy-functional polybutadienes.

Polyester polyols prepared, for example, from dihydric to trihydric alcohols such as, for example, 1,2-ethanediol, diethylene glycol, 1,2-propanediol, dipropylene glycol, 1,4-butanediol, 1,5-pentanediol, 1,6-hexanediol, neopentyl glycol, glycerol, 1,1,1-trimethylolpropane or mixtures of the aforementioned alcohols with organic dicarboxylic acids or their anhydrides or esters, such as, for example, succinic acid, glutaric acid, adipic acid, suberic acid, sebacic acid, dodecanedicarboxylic acid, maleic acid, fumaric acid, phthalic acid, isophthalic acid, terephthalic acid, and hexahydrophthalic acid or mixtures of the aforementioned acids, and also polyester polyols formed from lactones such as ε-caprolactone, for example.

Polycarbonate polyols of the kind obtainable by reacting, for example, the abovementioned alcohols—those used to synthesize the polyester polyols—with dialkyl carbonates, diaryl carbonates or phosgene.

Polyacrylate and polymethacrylate polyols.

These stated polyols have an average molecular weight of 250 to 30 000 g/mol, in particular of 1000 to 30 000 g/mol, and an average OH functionality in the range from 1.6 to 3.

In addition to these stated polyols it is possible to use dihydric or polyhydric alcohols of low molecular weight, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexane-dimethanol, hydrogenated bisphenol A, dimeric fatty alcohols, 1,1,1-tri-methylolethane, 1,1,1-trimethylolpropane, glycerol, pentaerythritol, sugar alcohols, and other higher polyhydric alcohols, low molecular weight alkoxylation products of the aforementioned dihydric and polyhydric alcohols, and also mixtures of the aforementioned alcohols, when preparing the polyurethane polymer.

Polyisocyanates used for preparing a polyurethane polymer of this kind are commercially customary polyisocyanates. Examples that may be mentioned include the following polyisocyanates, which are well known in polyurethane chemistry:

tolylene 2,4- and 2,6-diisocyanate (TDI) and any desired mixtures of these isomers, diphenylmethane 4,4'-diisocyanate (MDI), the positionally isomeric diphenylmethane diisocyanates, phenylene 1,3- and 1,4-diisocyanate, 2,3,5,6-tetramethyl-1,4-diisocyanatobenzene, hexamethylene 1,6-diisocyanate (HDI), 2-methylpentamethylene 1,5-diisocyanate, 2,2,4- and 2,4,4-trimethyl-hexamethylene 1,6-diisocyanate (TMDI), dodecamethylene 1,12-diisocyanate, cyclohexane 1,3- and 1,4-diisocyanate and any desired mixtures of these isomers, 1-isocyanato-3,3,5-trimethyl-5-isocyanatomethylcyclohexane (isophorone diisocyanate or IPDI), perhydrodiphenylmethane 2,4'- and 4,4'-diisocyanate (HMDI), 1,4-diisocyanato-2,2,6-trimethylcyclohexane (TMCDI), m- and p-xylylene diisocyanate (XDI), tetramethylxylylene 1,3- and 1,4-diisocyanate (TMXDI), 1,3- and 1,4-bis(isocyanatomethyl)cyclohexane, and also oligomers and polymers of the aforementioned isocyanates, and also any desired mixtures of the aforementioned isocyanates. Particular preference is given to MDI, TDI, HDI, and IPDI, and mixtures thereof. Maximum preference is given to MDI and TDI and mixtures thereof.

Further possible constituents of the moisture-curing polymer composition, particularly of the moisture-curing polyurethane composition, are polyaldimines as already described in connection with the preparation of the aldiminoalkylsilanes ALS. Preference is given in this context to polyaldimines which are prepared by reacting a primary aliphatic polyamine with an aldehyde, in particular an aldehyde ALD of the formula (II), with removal of water. It is especially advantageous to use polyaldimines of this kind in the form of the above-described solutions of aldiminoalkylsilanes ALS in polyaldimines.

As further possible constituents of the moisture-curing polymer composition, particularly of the moisture-curing polyurethane composition, mention may be made by way of example of the following auxiliaries and adjuvants, which are well known in the polyurethane industry:

Plasticizers, examples being esters of organic carboxylic acids or their anhydrides, phthalates, dioctyl phthalate or diisodecyl phthalate for example, adipates, dioctyl adipate for example, sebacates, organic phosphoric and sulfonic esters, polybutenes and other non-isocyanate-reactive compounds; reactive diluents and crosslinkers, examples being polyhydric alcohols, polyamines, polyaldimines, polyketimines or aliphatic isocyanates, examples being 1,6-hexamethylene diisocyanate, 2,2,4- and 2,4,4-trimethylhexamethylene 1,6-diisocyanate, dodecamethylene 1,12-diisocyanate, cyclohexane 1,3- and 1,4-diisocyanate, and any desired mixtures of these isomers, 1-isocyanato-3,3,5-trimethyl-5-isocyanatomethylcyclohexane (isophorone diisocyanate or IPDI), perhydrodiphenylmethane 2,4'- and 4,4'-diisocyanate, tetramethylxylylene 1,3- and 1,4-diisocyanate, isocyanurates of these isocyanates, oligomers and polymers of these isocyanates, and also their adducts with polyols; organic and inorganic fillers, examples being ground or precipitated calcium carbonates, which if appropriate have been coated with stearates, especially finely divided coated calcium carbonate, carbon blacks, kaolins, aluminas, silicas, and PVC powders or hollow beads; fibers, of polyethylene for example; pigments; catalysts for the reaction of the isocyanate groups, examples being organotin compounds such as dibutyltin diacetate, dibutyltin dilaurate, dioctyltin dicarboxylate, dibutyltin dichloride, dibutyltin diacetylacetonate, alkyltin thioesters, organobismuth compounds or bismuth complexes, compounds containing amino groups, such as 2,2'-dimorpholinodiethyl ether, for example, and other catalysts typical in polyurethane chemistry; catalysts for the hydrolysis of aldimino groups, examples being organic carboxylic acids such as benzoic acid or salicylic acid, organic carboxylic anhydrides such as phthalic anhydride or hexahydrophthalic anhydride, silyl esters of organic carboxylic acids, organic sulfonic acids such as p-toluenesulfonic acid or 4-dodecylbenzenesulfonic acid, or other organic or inorganic acids, or mixtures of the aforementioned acids; rheology modifiers such as, for example, thickeners, examples being urea compounds, polyamide waxes, bentonites or pyrogenic silicas; further adhesion promoters additional to the aldiminoalkylsilanes ALS of the invention, particularly silanes such as alkylsilanes, epoxyalkylsilanes, vinylsilanes, methacryloyloxyalkylsilanes and isocyanatoalkylsilanes, and also oligomeric forms of these silanes; dryers, examples being p-tosyl isocyanate and other reactive isocyanates, orthoformic esters, calcium oxide or molecular sieves; heat, light, and UV stabilizers; flame retardants; surface-active substances, examples being wetting agents, flow control agents, devolatilizers or defoamers; fungicides or substances which inhibit fungal growth; and also further substances typically employed in the polyurethane industry.

The polymer composition may further comprise polymers which contain hydrolyzable silane groups. Examples that may be mentioned of polymers of this kind containing silane groups include the following: reaction products of polyurethane polymers containing isocyanate groups with isocyanate-reactive organosilanes such as mercaptoalkylsilanes or aminoalkylsilanes, for example, described for example in U.S. Pat. No. 3,632,557, particularly the reaction products of polyurethane polymers containing isocyanate groups with Michael adducts of aminoalkylsilanes and maleic or fumaric diesters, described for example in EP 0 403 921; products of hydrosilylation reactions of polymers having terminal double bonds, particularly of allyl-terminated polyoxyalkylene polymers, with alkoxysilanes, described for example in U.S. Pat. No. 3,971,751 and U.S. Pat. No. 6,207,766; reaction products of polymers containing active hydrogen atoms, in the form for example of hydroxyl or mercapto groups, with isocyanatoalkylsilanes, described for example in U.S. Pat. No. 4,345,053 and U.S. Pat. No. 5,990,257; polymers containing 3-(N-silylalkyl)aminopropenoate groups, which represent reaction products of aminoalkylsilanes with polymers containing 3-oxopropanoate groups, and are described for example in WO 2004/056905.

The polymer composition may further comprise polymers which contain isocyanate groups and silane groups.

The amount of aldiminoalkylsilane ALS in the moisture-curing polymer composition, particularly the moisture-curing polyurethane composition, is 0.01%-10% by weight, preferably 0.1%-5% by weight, in particular 0.25%-2.5% by weight.

The moisture-curing polymer composition described, particularly the moisture-curing polyurethane composition, is prepared and stored in the absence of moisture and can be stored in a suitable pack or arrangement, such as in a drum, a pouch or a cartridge, for example, prior to its use, for a period of several months up to one year or more, without losing its usefulness.

The moisture-curing polymer composition described, particularly the moisture-curing polyurethane composition, is suitable, for example, as a sealant of all kinds, for the purpose, for example, of sealing joints in construction, as an adhesive for the bonding of a variety of substrates, for the purpose, for example, of bonding components in the manufacture of automobiles, rail vehicles, boats or other industrial goods, and also as a coating or covering for a variety of articles and/or variable substrates. On the basis of its capacity to be low in odor or odorless and not to release intensely odorous substances, it is especially suitable for adhesive and sealing applications in the interior of enclosed spaces, such as in the interior of buildings or vehicles, for example, where exacting requirements are imposed on the materials employed in terms of odor, since the occurrence of an intense or unpleasant odor would make it more difficult if not impossible to use the finished article within a reasonable time. Preferred coatings are protective paint coatings, sealing coatings, and other protective coatings. Among the coverings, floor coverings are particularly preferred. Such coverings are produced by pouring, typically, a reactive composition onto the base and leveling it, where it cures to form a floor covering. Floor coverings of this kind are used, for example, for offices, living areas, hospitals, schools, warehouses, car parks, and other private or industrial applications. Since many of these applications involve large surface areas, even a low level of release of substances from the covering can lead to occupational hygiene difficulties and/or odor nuisance, even when the application involved is outdoors. Nevertheless, a large proportion of floor coverings are applied in the interior sector, and so particular importance is placed here on a low odor development.

Suitable substrates for application of the moisture-curing polymer composition described, especially of the moisture-curing polyurethane composition, are, for example, inorganic substrates such as glass, glass ceramic, concrete, mortar, brick, tile, plaster, and natural stone such as granite or marble, for example; metals such as aluminum, steel, nonferrous metals, galvanized metals; organic substrates such as wood, plastics such as PVC, polycarbonates, PMMA, polyesters, epoxides; coated substrates such as powder-coated metals, for example; and also paints and varnishes, especially automotive topcoats. Preferred substrates are glass, glass ceramic, concrete, natural stone, aluminum, and automotive topcoats.

The moisture-curing polymer composition, especially the moisture-curing polyurethane composition, is contacted here at least partially with the surface of the substrate in question. Preference is given to uniform contacting in the form of an adhesive or sealant, a coating or a covering, specifically in those areas which for service require a bond in the form of an adhesive bond or seal or else whose surface is to be covered over. It may well be necessary, prior to the contacting step, to subject the substrate or article to be contacted to a physical pretreatment, by means for example of abrading, sandblasting, brushing or the like, or by treatment with cleaning products or solvents. The application of an adhesion promoter composition, in the form of a primer for example, is unnecessary, however, owing to the aldiminoalkylsilane ALS present in the moisture-curing polymer composition, especially in the moisture-curing polyurethane composition.

In the context of the application of the moisture-curing polymer composition, especially the moisture-curing polyurethane composition, it comes into contact with moisture, whereupon not only the isocyanate groups but also other compounds reactive with water react with water. Where the moisture-curing polymer composition comprises polyaldimines, the hydrolysis products thereof react with some of the isocyanate groups before they can react with water. As a consequence of this and further reactions, the composition cures. At the same time, the aldiminoalkylsilane ALS present in the moisture-curing polymer composition undergoes hydrolysis in the manner already described, and contributes, accordingly, to an improvement in the adhesion to the substrate. The aldehyde ALD liberated in the course of the hydrolysis preferably remains substantially completely in the cured polymer composition. Either the water needed for curing can come from the air (atmospheric moisture) or the polymer composition can be contacted with a water-containing component, for example by being brushed, using a smoothing agent, for example, by being sprayed, or by means of immersion methods, or a water-containing component can be added to the polymer composition, in the form for example of a water-containing paste, which is mixed in, for example, via a static mixer.

As already mentioned, the aldiminoalkylsilanes ALS of the invention can also be present in the form of a constituent of adhesion promoter compositions such as adhesion promoter solutions, pretreatment agents, undercoats, cleaning products or primers. In addition to an aldiminoalkylsilane ALS, adhesion promoter compositions of this kind include at least one solvent and also, optionally, further components typically employed in the coatings industry.

Examples of suitable solvents for an adhesion promoter composition of this kind include the following:

Alcohols such as, for example, methanol, ethanol, isopropanol or butanol; ketones such as, for example, acetone, methyl ethyl ketone, diisobutyl ketone, acetonylacetone, mesityl oxide, and also cyclic ketones such as methylcyclohexanone and cyclohexanone, for example; esters, examples being acetates such as ethyl acetate, propyl acetate or butyl acetate, formates, propionates or malonates; ethers such as, for example, ketone ethers, ester ethers, and dialkyl ethers such as diisopropyl ether, diethyl ether, dibutyl ether, diethylene glycol diethyl ether, and ethylene glycol diethyl ether; aliphatic and aromatic hydrocarbons such as, for example, toluene, xylene, heptane, octane, and also various petroleum fractions such as naphtha, white spirit, petrol ether or benzine; halogenated hydrocarbons such as methylene chloride, for example; and also N-alkylated lactams such as N-methylpyrrolidone, for example.

As a further component in the adhesion promoter composition there may be a binder present, mention being made in particular of polyurethane polymers containing isocyanate groups and/or silane groups; or there may be polyisocyanates present, examples being tris(4-isocyanatophenyl)methane, tris(4-isocyanatophenyl) thiophosphate, the aforementioned monomeric MDI, TDI, HDI, and IPDI, and also oligomers, polymers and copolymers of these monomers, such as polymeric HDI, polymeric MDI, available commercially for example as Voranate® M 229 (Dow), Desmodur® VL R 20 (Bayer), or allophanates, biurets, uretdiones, and isocyanurates of these monomers, especially HDI biurets, such as those available commercially, for example, as Desmodur® N-100 (Bayer), Luxate® HDB 9000 (Lyondell/Bayer), HDI trimers, such as those available commercially, for example, as Desmodur® N-3300 (Bayer), Desmodur® N-3600 (Bayer), Luxate® HT 2000 (Lyondell/Bayer), Desmodur® XP 2410, HDI dimers, such as those available commercially, for example, as Desmodur® N-3400 (Bayer), Luxate® HD 100 (Lyondell/Bayer), IPDI trimers, such as those available commercially, for example, as Desmodur® Z 4470 (Bayer), Vestanat® T 1890 (Degussa), Luxate® IT 1070 (Lyondell/Bayer), HDI and IPDI allophanates, TDI trimers, such as those available commercially, for example, as Desmodur® IL (Bayer), TDI adducts, such as those available commercially, for example, as Desmodur® L (Bayer), and TDI/HDI polymers, such as those available commercially, for example, as Desmodur® HL (Bayer), Polurene® IK D (Sapici), and Hartben AM 29 (Benasedo).

As further water-reactive compounds it is possible for example for polyaldimines, polyketimines, oxazolidines, further organoalkoxysilanes such as, for example, aminoalkylsilanes, aminosilanes containing secondary amino groups, epoxyalkylsilanes, mercaptoalkylsilanes, vinylsilanes, ureidoalkyl-silanes, methacryloyloxyalkylsilanes, alkylsilanes, and isocyanatoalkylsilanes to be present in the adhesion promoter composition, it being possible for these compounds to act as crosslinkers and/or as dryers. Aminosilanes and/or mercaptoalkylsilanes can also be present in the form of adducts with epoxyalkylsilanes, for example with 3-glycidyloxypropylsilanes. Particularly preferred additional constituents of the adhesion promoter composition are aminoalkylsilanes AS of the formula (I).

As a constituent of the adhesion promoter composition it is likewise possible to use catalysts for the hydrolysis not only of aldimino groups but also of silane groups, in the form, for example, of organic carboxylic acids such as benzoic acid or salicylic acid, organic carboxylic anhydrides such as phthalic anhydride or hexahydrophthalic anhydride, silyl esters of organic carboxylic acids, organic sulfonic acids such as p-toluenesulfonic acid or 4-dodecylbenzenesulfonic acid, or other organic or inorganic acids, or mixtures of the aforementioned acids; and also catalysts for the reaction of isocyanate groups, examples being tin compounds such as tin(II) octoate, monobutyltin trichloride, dibutyltin dichloride, dibutyltin oxide, dibutyltin diacetate, dibutyltin dilaurate, dibutyltin diacetylacetonate, dibutyltin dicarboxylates, dioctyltin dicarboxylates, alkyltin thioesters, bismuth compounds such as bismuth(III) octoate, bismuth(III) neodecanoate, zinc compounds such as zinc(II) octoate, and also compounds containing amino groups, such as, for example, 2,2'-dimorpholinodiethyl ether, 1,4-diazabicyclo[2.2.2]octane, 1,8-diazabicyclo[5.4.0]undec-7-ene; and also further catalysts such as titanates and zirconates.

In addition it is possible to use additives, fillers and wetting agents which are typical in primer chemistry. Nonlimiting examples thereof are silicas, talc, carbon black, organic and inorganic pigments, stabilizers, bentonites, and also chemical and physical dryers.

The adhesion promoter composition described is prepared and stored in the absence of moisture.

The adhesion promoter composition described is used as a tie between a substrate and a polymer composition, such as an adhesive, sealant or coating, for example. In order to obtain a reliable development of adhesion to a substrate on the part of the adhesion promoter composition, the latter composition must have a certain minimum time span available, referred to as the "flash-off time", before the polymer composition is applied. The time between the application of the adhesion promoter composition and the application of the polymer composition, and within which reliable development of adhesion to the substrate is still ensured, is called the "open time" and is usually limited. If the open time is exceeded, development of adhesion to the substrate is either incomplete or does not take place at all. An adhesion promoter composition comprising an aldiminoalkylsilane ALS has a long open time of at least one week. The long open time is made possible by virtue of the fact that the aldimino groups of the aldiminoalkylsilanes ALS, in contrast to the amino groups of aminoalkylsilanes AS, react not at all or only to a very small extent with the carbon dioxide present in the air, and so are available for substantially longer for the reaction with a subsequently applied polymer composition.

Suitable substrates for use of the adhesion promoter composition described are, for example, inorganic substrates such as, for example, glass, glass ceramic, concrete, mortar, brick, tile, plaster and natural stone such as granite or marble; metals such as aluminum, steel, nonferrous metals, galvanized metals; organic substrates such as wood, plastics such as PVC, polycarbonates, PMMA, polyesters, epoxides; coated substrates such as, for example, powder-coated metals; and also paints and varnishes, especially automotive topcoats. Preferred substrates are glass, glass ceramic, concrete, natural stone, aluminum, and automotive topcoats.

It is of advantage if the substrates are pretreated prior to application. Suitable methods of pretreatment are physical and/or chemical in nature and include, for example, abrading, sandblasting, brushing or the like, or treating with cleaning products or solvents.

The adhesion promoter composition is applied to the substrate by means of brush, felt, cloth or sponge. This application can be carried out manually or automatically, in particular by means of robots. In addition it is also possible for two or more coats of the adhesion promoter composition to be applied.

The adhesion promoter composition described is used with advantage as a tie for adhesives, sealants or coatings such as, for example, floor coverings, especially moisture-curing adhesives or sealants based on polyurethanes containing isocyanate groups and/or silane groups. This adhesion promoter composition is especially suitable for applications requiring a long open time.

The adhesion promoter composition reacts on contact with water, in the form, for example, of atmospheric moisture, the aldiminoalkylsilane ALS undergoing hydrolysis in the way already described and thus contributing to an improvement in adhesion to the substrate, and other components present in the adhesion promoter composition that are reactive with water, such as, compounds containing isocyanate groups or silane groups, for example, likewise react with water.

Applied atop the adhesion promoter composition, observing a minimum flash-off time and a maximum open time, is a polymer composition in the form of an adhesive, sealant, a coating or a covering, the adhesion promoter composition contacted with water serving as a tie between the substrate and the cured polymer composition.

The solvents present in the adhesion promoter composition evaporate, either completely or partially within the flash-off time, or after the polymer composition has been applied, evaporation taking place through said composition and into the ambient environment.

EXAMPLES

Description of Measurement Methods

The infrared spectra were recorded on a Perkin-Elmer 1600 FT-IR instrument (horizontal ATR measuring unit with ZnSe crystal); the samples were applied in undiluted form as films. The absorption bands are reported in wavenumbers ($cm^{-1}$) (measurement window: 4000-650 $cm^{-1}$).

$^1$H NMR spectra were measured on a Bruker DPX-300 spectrometer at 300.13 MHz; the chemical shifts, δ, are expressed in ppm relative to internal tetramethylsilane (TMS), coupling constants J are indicated in Hz.

The viscosity was measured at 20° C. on a cone/plate viscometer from Haake (PK100/VT-500).

Preparation and Characterization of Aldiminoalkylsilanes

Example 1

Aldiminoalkylsilane ALS1

In a round-bottomed flask 15.0 g of 3-aminopropyltrimethoxysilane (Silquest® A-1110, OSi Crompton) were dissolved under a nitrogen atmosphere in 25 ml of dry methanol. About 2 g of activated 4 Å molecular sieve were added thereto and the flask was placed in a waterbath. 13.3 g of 2,2-dimethyl-3-acetoxypropanal were added from a dropping funnel over the course of 10 minutes with vigorous stirring, the temperature of the reaction mixture not exceeding 30° C. Thereafter the molecular sieve was filtered off and the volatile constituents were removed under reduced pressure (10 mbar, 70° C.). This gave a colorless, clear liquid which was highly mobile at room temperature, had a fruity aroma and had an aldimine content, determined as amine content, of 3.23 mmol $NH_2/g$.

IR: 2972, 2941, 2876sh, 2839, 1740 (C=O), 1668 (C=N), 1471, 1410, 1396, 1374, 1240, 1190, 1082, 1037, 929, 874, 816, 771sh, 698.

$^1$H NMR (CDCl$_3$, 300 K): δ 7.53 (s, 1H, CH=N), 4.02 (s, 2H, CH$_2$O), 3.57-3.53 (m, about 8H, CH$_2$Si—OCH and CH$_2$Si—O—Si—OCH$_3$), 3.35 (m, 2H, NCH$_2$), 2.05 (s, 3H, CH$_3$CO), 1.69 (m, 2H, CH$_2$CH$_2$N), 1.10 (s, 6H, C(CH$_3$)$_2$—CH$_2$O), 0.59 (m, 2H, CH$_2$Si).

Example 2

Aldiminoalkylsilane ALS2

In a round-bottomed flask 50.0 g of 3-aminopropyltrimethoxysilane (Silquest® A-1110, OSi Crompton) were dissolved under a nitrogen atmosphere in 40 ml of dry methanol. About 5 g of activated 4 Å molecular sieve were added thereto and the flask was placed in a waterbath. 50.4 g of 2,2-dimethyl-3-isobutyroxypropanal were added from a dropping funnel over the course of 15 minutes with vigorous stirring, the temperature of the reaction mixture not exceeding 31° C. Thereafter the molecular sieve was filtered off and the volatile constituents were removed under reduced pressure (10 mbar, 70° C.). This gave a colorless, clear liquid which was highly mobile at room temperature, had a fruity aroma and had an aldimine content, determined as amine content, of 2.97 mmol $NH_2/g$.

IR: 2972, 2937, 2876, 2839, 1735 (C=O), 1668 (C=N), 1470, 1410, 1386, 1365, 1341, 1300, 1257, 1190, 1151, 1074, 996sh, 931, 917sh, 874, 816, 795sh, 763sh, 697.

$^1$H NMR (CDCl$_3$, 300 K): δ 7.54 (s, 1H, CH=N), 4.02 (s, 2H, CH$_2$O), 3.61-3.53 (m, about 8H, CH$_2$Si—OCH$_3$ and CH$_2$Si—O—Si—OCH$_3$), 3.37 (m, 2H, NCH$_2$), 2.55 (q×q, J=7.0, 1H, CH(CH$_3$)$_2$), 1.67 (m, 2H, CH$_2$CH$_2$N), 1.17-1.11 (m, 12H, CH(CH$_3$)$_2$ and C(CH)$_2$—CH$_2$O), 0.60 (m, 2H, CH$_2$Si).

Example 3

Aldiminoalkylsilane ALS3

A round-bottomed flask with reflux condenser and water separator (Dean Stark) was charged with 52.7 g of formaldehyde (37% in water, methanol-free), 46.8 g of isobutyraldehyde, 100.0 g of lauric acid and 0.5 g of 4-toluenesulfonic acid and placed under a nitrogen atmosphere. The mixture was heated in an oil bath with vigorous stirring, whereupon water began to separate out. After four hours the apparatus was evacuated under a waterjet vacuum. A total of around 48 ml of distillate collected in the separator. The reaction mixture (aldehyde) was cooled to room temperature. In a second round-bottomed flask, 78.8 g of 3-aminopropyltrimethoxysilane (Silquest® A-1110, OSi Crompton) were dissolved under a nitrogen atmosphere in 80 g of anhydrous methanol. About 10 g of activated 4 Å molecular sieve were added thereto and the flask was placed in a waterbath. The aldehyde described above was added dropwise via a steel cannula over the course of 30 minutes with vigorous stirring, the temperature of the reaction mixture not exceeding 32° C. Thereafter the molecular sieve was filtered off and the volatile constituents were removed under reduced pressure (10 mbar, 70° C.). This gave an amber-colored, clear oil which was highly mobile at room temperature, was completely odorless and had an aldimine content, determined as amine content, of 2.10 mmol $NH_2$/g.

IR: 2950sh, 2923, 2852, 1737 (C=O), 1668 (C=N), 1466, 1416, 1394, 1374, 1343, 1301, 1248, 1188, 1156, 1085, 1036sh, 930, 873, 818, 785sh, 721, 698.

$^1$H NMR (CDCl$_3$, 300 K): δ 7.53 (s, 1H, CH=N), 4.02 (s, 2H, CH$_2$O), 3.56-3.53 (m, about 8H, CH$_2$Si—OCH$_3$ and CH$_2$Si—O—Si—OCH$_3$), 3.37 (m, 2H, NCH$_2$), 2.30 (t, J=7.5, 2H, CH$_2$CO), 1.62 (m, 4H, CH$_2$CH$_2$N and CH$_2$CH$_2$CO), 1.26-1.23 (m, 16H. CH$_3$—(CH$_2$)$_8$—CH$_2$CH$_2$CO), 1.10 (s, 6H, C(CH$_3$)$_2$—CH$_2$O), 0.88 ("t", 3H, J=6.6, CH$_3$—(CH$_2$)$_{10}$—CO), 0.59 (m, 2H, CH$_2$Si).

Example 4

Aldiminoalkylsilane ALS4

In a round-bottomed flask 30.0 g of (3,3-dimethyl-4-amino)butyltrimethoxysilane (Silquest® A-1637, OSi Crompton) were dissolved under a nitrogen atmosphere in 30 ml of dry methanol. About 5 g of activated 4 Å molecular sieve were added thereto and the flask was placed in a waterbath. 24.5 g of 2,2-dimethyl-3-isobutyroxypropanal were added from a dropping funnel over the course of 15 minutes with vigorous stirring, the temperature of the reaction mixture not exceeding 28° C. Thereafter the molecular sieve was filtered off and the volatile constituents were removed under reduced pressure (10 mbar, 70° C.). This gave a colorless, clear liquid which was highly mobile at room temperature, had a fruity aroma and had an aldimine content, determined as amine content, of 2.97 mmol $NH_2$/g.

IR: 2964, 2837, 1735 (C=O), 1670 (C=N), 1470, 1385, 1364, 1340, 1190, 1151, 1081, 1032, 992, 936, 887, 824, 788, 759, 677.

Example 5

Aldiminoalkylsilane ALS5

In a round-bottomed flask 14.3 g of 2,2-dimethyl-3-isobutyroxypropanal were dissolved under a nitrogen atmosphere in 20 ml of dry ethanol. About 2 g of activated 4 Å molecular sieve were added thereto and the flask was placed in a waterbath. 20.0 g of N-(2-aminoethyl)-3-aminopropyltriethoxysilane (Silquest® Y-11763, OSi Crompton) were added from a dropping funnel over the course of 15 minutes with vigorous stirring, the temperature of the reaction mixture not exceeding 28° C. Thereafter the molecular sieve was filtered off and the volatile constituents were removed under reduced pressure (10 mbar, 70° C.). This gave a colorless, clear oil which was highly mobile at room temperature, had a fruity aroma and had an aldimine content, determined as amine content, of 4.33 mmol $NH_2$/g.

IR: 3337 (N—H), 2972, 2929, 2881, 2840sh, 2804sh, 1732 (C=O), 1667 (C=N), 1470, 1408sh, 1389, 1365, 1344, 1305, 1260, 1192, 1156, 1097, 1074, 995, 954, 898, 789, 774, 690.

Example 6

Aldiminoalkylsilane ALS6

A round-bottomed flask with reflux condenser and water separator (Dean Stark) was charged with 10.8 g of formaldehyde (37% in water, methanol-free), 9.6 g of isobutyraldehyde, 20.6 g of lauric acid and 0.1 g of 4-toluenesulfonic acid and placed under a nitrogen atmosphere. The mixture was heated in an oil bath with vigorous stirring, whereupon water began to separate out. After four hours the apparatus was evacuated under a waterjet vacuum. A total of around 9.5 ml of distillate collected in the separator. The reaction mixture (aldehyde) was cooled to room temperature. In a second round-bottomed flask, 22.9 g of N-(2-aminoethyl)-3-aminopropyltriethoxysilane (Silquest® Y-11763, OSi Crompton) were dissolved under a nitrogen atmosphere in 20 g of anhydrous ethanol. About 2 g of activated 4 Å molecular sieve were added thereto and the flask was placed in a waterbath. The aldehyde described above was added dropwise via a steel cannula over the course of 15 minutes with vigorous stirring, the temperature of the reaction mixture not exceeding 26° C. Thereafter the molecular sieve was filtered off and the volatile constituents were removed under reduced pressure (10 mbar, 70° C.). This gave a brown-orange, clear oil which was of low mobility at room temperature, was odorless and had an aldimine content, determined as amine content, of 3.21 mmol $NH_2$/g.

IR: 3337 (N—H), 2951sh, 2921, 2852, 1737 (C=O), 1650, 1466, 1408, 1392, 1365, 1295, 1165, 1092sh, 1076, 953, 840, 784, 721.

Aldiminoalkylsilane ALS7

Comparative Example

In a round-bottomed flask 50.0 g of 3-aminopropyltrimethoxysilane (Silquest® A-1110, OSi Crompton) were dissolved under a nitrogen atmosphere in 100 ml of dry methanol. About 10 g of activated 4 Å molecular sieve were added thereto and the flask was placed in a waterbath. 32.6 g of benzaldehyde were added from a dropping funnel over the course of 30 minutes with vigorous stirring, the temperature of the reaction mixture not exceeding 35° C. Thereafter the molecular sieve was filtered off and the volatile constituents were removed under reduced pressure (10 mbar, 70° C.). This gave a colorless, clear liquid which was highly mobile at room temperature, had a intense bitter almond oil aroma and had an aldimine content, determined as amine content, of 3.73 mmol $NH_2$/g.

IR: 3060, 3026, 2938, 2838, 1704, 1645 (C=N), 1580, 1493, 1451, 1411, 1377, 1343, 1310, 1250, 1189, 1076, 916, 881, 814, 753, 692.

Aldiminoalkylsilane ALS8

Comparative Example

In a round-bottomed flask 50.0 g of 3-aminopropyltrimethoxysilane (Silquest® A-1110, OSi Crompton) were dissolved under a nitrogen atmosphere in 100 ml of dry methanol. About 10 g of activated 4 Å molecular sieve were added thereto and the flask was placed in a waterbath. 32.6 g of isobutyraldehyde were added from a dropping funnel over the course of 45 minutes with vigorous stirring, the temperature of the reaction mixture not exceeding 35° C. Thereafter the molecular sieve was filtered off and the volatile constituents were removed under reduced pressure (10 mbar, 70° C.). This gave a colorless, clear liquid which was highly mobile at room temperature, had a pungent odor and had an aldimine content, determined as amine content, of 4.49 mmol $NH_2$/g.

IR: 2962, 2936, 2871, 2838, 1735, 1670 (C=N), 1466, 1410, 1386, 1366, 1343, 1302, 1249, 1192, 1082, 952, 872, 814, 695.

Example 7

Aldiminoalkylsilane ALS3 in Polyaldimine

A round-bottomed flask was charged with 10.09 of alpha, omega-polyoxypropylenediamine (Jeffamine® D-230, Huntsman; amine content=8.29 mmol $NH_2$/g) and 2.8 g of 3-aminopropyltrimethoxysilane (Silquest® A-1110, OSi Crompton) and placed under a nitrogen atmosphere. The flask was placed in a waterbath. 30.5 g of freshly distilled 2,2-dimethyl-3-lauroyloxypropanal were added from a dropping funnel over the course of 20 minutes with vigorous stirring, the temperature of the reaction mixture not exceeding 32° C. Thereafter the volatile constituents were removed under reduced pressure (10 mbar, 70° C.). This gave a colorless, clear and almost odorless liquid which was highly mobile at room temperature, and had an aldimine content, determined as amine content, of 2.37 mmol $NH_2$/g. Analysis by liquid chromatography showed a very low level of condensation products.

IR: 2957, 2922, 2852, 1737 (C=O), 1666 (C=N), 1466, 1418, 1374, 1343, 1249, 1156, 1107, 1020, 930, 873, 822, 722.

Preparation and Testing of Moisture-Curing Polyurethane Compositions Comprising Aldiminoalkylsilanes Examples 8 to 20

A polypropylene beaker with screw top was charged with about 50 g of polyurethane polymer PP1, whose preparation is described below, and placed under dry nitrogen. Added thereto was 1.0% by weight (based on the polyurethane polymer PP1) in each case of the aldiminoalkylsilanes listed in Table 1 and, if listed in Table 1, further additives were added, and these components were mixed in homogeneously using a centrifugal mixer (SpeedMixer™ DAC 150, FlackTek Inc.).

For the determination of the storage stability the polyurethane compositions were dispensed immediately into internally coated aluminum tubes, which were given an airtight seal and stored in an oven at 60° C. The viscosity of the polyurethane compositions was measured a first time after 12 hours and a second time after 7 days of storage. The storage stability is given by the proportion of the two viscosity measurements (relative increase in the viscosity of the samples stored 7 days in relation to the viscosity of the samples stored 12 hours). The results are set out in Table 2.

For the test of the adhesion the polyurethane compositions of Examples 8 to 20 described above were freshly prepared again and stored in the tube at room temperature (no oven storage). For each example the following procedure was then carried out:

A glass plate (float glass; Rocholl, Schönbrunn, Germany) measuring 10×15 cm had Distanzband-J (Karochemie) tape stuck lengthwise on the air side (testing with UV light, wavelength 254 nm) in such a way as to give three glass tracks of 1.5×15 cm. The tracks were wiped three times each with a paper towel moistened with acetone. After a flash-off time of 5 minutes, the polyurethane composition from the tube was applied to the glass tracks in a layer thickness of 2 to 3 mm, ensuring that it did not flow off over the edge of the glass. The glass plate was stored flat for 7 days under standard conditions (23±1° C., 50±5% relative humidity), in the course of which the polyurethane composition cured. Thereafter the first track was tested for adhesion. The glass plate was then stored in water at room temperature for 7 days and left to dry, and the second track was tested for adhesion. Subsequently the glass plate was stored for 7 days under hot, humid conditions (70° C., 100% humidity) and the third track was tested for adhesion.

The test for adhesion was carried out as follows:

An incision was made into one end of the track of the cured polyurethane composition ("bead"), just above the glass surface (bondline). The incised end of the bead was held by hand and then pulled carefully and slowly from the glass surface with a peeling action, in the direction of the other end of the bead. If, in the course of this removal, the adhesion was so strong that the end of the bead threatened to tear off when being pulled, a cutter was used to apply a cut perpendicular to the bead-pulling direction, down to the bare glass surface, and in this way a section of the bead was detached. Cuts of this kind were repeated, if necessary, on continued pulling, at a distance of 2 to 3 mm. In this way the entire bead was pulled and/or cut from the glass track. The adhesive properties were evaluated on the basis of the cured polyurethane composition which remained on the surface after the bead had been removed (cohesive fracture), this being accomplished by estimating the cohesive fraction of the bond area, in accordance with the following scale:

1=more than 95% cohesive fracture
2=75-95% cohesive fracture
3=25-75% cohesive fracture
4=less than 25% cohesive fracture
5=0% cohesive fracture (purely adhesive fracture)

Test results with cohesive fracture values of less than 75% are considered inadequate.

The results of the tests are set out in Table 2.

Polyurethane polymer PP1 was prepared as follows:

845 g of Polyol Acclaim® 4200 N (Bayer; polypropylene oxide diol, OH number 28.5 mg KOH/g) and 115 g of 4,4'-methylenediphenyl diisocyanate (MDI; Desmodur® 44 MC L, Bayer) were reacted by a known method at 80° C. to form an NCO-terminated polyurethane polymer. The reaction product had a free isocyanate group content, determined by titrimetry, of 1.96% by weight and a viscosity at 20° C. of 37 Pa·s.

TABLE 1

Constitution of the polyurethane compositions of Examples 8 to 20.

| Example | Aldiminoalkylsilane (% by weight[a]) | further additives (% by weight[a]) |
|---|---|---|
| 8 | ALS1 (1.0) | — |
| 9 | ALS2 (1.0) | — |
| 10 | ALS2 (1.0) | Salicylic acid (0.1) |
| 11 | ALS3 (1.0) | — |
| 12 | ALS4 (1.0) | — |
| 13 | ALS5 (1.0) | — |
| 14 | ALS5 (1.0) | Benzoyl chloride (0.1) |
| 15 | ALS6 (1.0) | — |
| 16 | ALS3 (1.0) | Polyaldimine[b] (9.0), salicylic acid (0.1) |
| 17 (Ref.)[c] | — | — |
| 18 (Ref.)[c] | — | Polyaldimine[b] (9.0), salicylic acid (0.1) |

TABLE 1-continued

Constitution of the polyurethane compositions of Examples 8 to 20.

| Example | Aldiminoalkylsilane (% by weight[a]) | further additives (% by weight[a]) |
|---|---|---|
| 19 (Comp.)[d] | ALS7 (1.0) | — |
| 20 (Comp.)[d] | ALS8 (1.0) | — |

[a]based on polyurethane polymer PP1
[b]dialdimine formed from 2,2-dimethyl-3-lauroyloxypropanal and 1,3-xylylenediamine
[c]Reference examples without aldiminoalkylsilane
[d]Comparative Examples in accordance with the prior art

TABLE 2

Storage stability and adhesion to glass of the polyurethane compositions of Examples 8 to 20

| Example | Viscosity increase in %[a] | Adhesion after storage under standard conditions | Adhesion after storage in water | Adhesion after storage under hot humid conditions |
|---|---|---|---|---|
| 8 | 10 | 1 | 1 | 1 |
| 9 | 3 | 1 | 1 | 1 |
| 10 | 4 | 1 | 1 | 1 |
| 11 | 2 | 1 | 1 | 1 |
| 12 | 2 | 1 | 1 | 1 |
| 13 | 22 | 1 | 1 | 1 |
| 14 | 18 | 1 | 5 | 1 |
| 15 | 17 | 1 | 1 | 1 |
| 16 | 4 | 1 | 1 | 1 |
| 17 (Ref.)[b] | 5 | 5 | 5 | 5 |
| 18 (Ref.)[b] | 1 | 5 | 5 | 5 |
| 19 (Comp.)[c] | 120 | 1 | 1 | 1 |
| 20 (Comp.)[c] | about 300 | 1 | 1 | 1 |

[a]= (viscosity after 7 d/viscosity after 12 h − 1) × 100%
[b]Reference examples without aldiminoalkylsilane
[c]Comparative examples in accordance with the prior art From Table 2 it can be seen that Examples 8 to 16, comprising aldiminoalkylsilanes of the invention, have not only very good storage stability (low increase in viscosity) but also very good adhesion to glass. Comparative Examples 19 and 20, which comprise prior art aldiminoalkylsilanes, likewise have good adhesion to glass, but their storage stability, with viscosity increases of well above 100%, is absent. The reference examples 17 and 18 without aldiminoalkylsilanes do not have adhesion to glass.

Preparation and Testing of Adhesion Promoter Compositions

Examples 21 to 26

1.0% by weight in each case of the aldiminoalkylsilanes of the invention was dissolved in methanol (ALS1 to ALS4) or ethanol (ALS5 and ALS6) and the resulting solution was tested as an adhesion promoter composition for improving the adhesion of polyurethane polymer PP1 to glass. The procedure adopted in this case was as follows:

As already described for Examples 8 to 20, Distanzband tape was stuck to three glass plates for each example. Each of the three glass tracks per plate was first wiped three times in each case with a paper towel moistened with acetone and was then wiped once in each case with a paper towel moistened with the respective adhesion promoter composition of Example 21 to 26. After a flash-off time of 15 minutes (1st glass plate) or an open time of 8 hours (2nd glass plate) and 7 days (3rd glass plate) the polyurethane polymer PP1 (Example 17, reference without aldiminoalkylsilane) was in each case applied, and storage, testing and assessment took place as already described for Examples 8 to 20.

The results of these tests are set out in Table 3.

TABLE 3

Adhesion to glass of polyurethane polymer PP1 (Example 17, Ref.), treated with the adhesion promoter compositions of Example 21 to 26, as a function of flash-off time and open time.

| Example | Adhesion promoter composition | Adhesion after storage under standard conditions[a] | Adhesion after storage in water[a] | Adhesion after storage under hot humid conditions[a] |
|---|---|---|---|---|
| 21 | ALS1 (1.0%[b] in MeOH) | 1/1/1 | 1/1/1 | 1/1/1 |
| 22 | ALS2 (1.0%[b] in MeOH) | 1/1/1 | 1/1/1 | 1/1/1 |
| 23 | ALS3 (1.0%[b] in MeOH) | 1/1/1 | 1/1/1 | 1/1/1 |
| 24 | ALS4 (1.0%[b] in MeOH) | 1/1/1 | 1/1/1 | 1/1/1 |
| 25 | ALS5 (1.0%[b] in EtOH) | 1/1/1 | 2/2/2 | 1/1/1 |
| 26 | ALS6 (1.0%[b] in EtOH) | 1/1/1 | 2/2/2 | 1/1/1 |

[a]1st number: glass plate with 15-minute flash-off time/2nd number: glass plate with 8-hour open time/3rd number: glass plate with 7-day open time
[b]% by weight The results of Table 3 show that polyurethane polymer PP1 (Example 17), which without pretreatment had no adhesion to glass (compare Table 2), exhibits distinctly improved adhesion after pretreatment with the inventive aldiminoalkylsilanes ALS1 to ALS6, and does so both for a flash-off time of 15 minutes and for an open time of 8 hours or of 7 days.

Preparation and Testing of Moisture-Curing Polyurethane Compositions as Adhesives

Examples 27 to 31

Examples 27 to 31 demonstrate the preparation of moisture-curing polyurethane compositions and their use as adhesives on glass.

Preparation of Base Composition PUR1:

In a vacuum mixer, 1750 g of polyurethane polymer PP2, 500 g of polyurethane polymer PP3, 800 g of carbon black, 800 g of calcined kaolin, 240 g of diisodecyl phthalate (DIDP; Palatinol® Z, BASF), 900 g of urea thickener and 10 g of p-tolylsulfonyl isocyanate (Zusatzmittel TI®, Bayer) were processed in the absence of moisture to give a lump-free, homogeneous paste, which was immediately filled into internally coated aluminum cartridges and given an airtight seal.

Polyurethane polymer PP2 was prepared as follows:

1290 g of Polyol Acclaim® 4200 N (polypropylene oxide diol, OH number 28.5 mg KOH/g; Bayer), 2580 g of Polyol Caradol® MD34-02 (polypropylene oxide-polyethylene oxide triol, OH number 35.0 mg KOH/g; Shell), 630 g of 4,4'-methylenediphenyl diisocyanate (MDI; Desmodur® 44 MC L, Bayer) and 500 g of diisodecyl phthalate (DIDP; Palatinol® Z, BASF) were reacted by a known method at 80° C. to form an NCO-terminated polyurethane polymer. The reaction product had a free isocyanate group content, determined by titrimetry, of 2.07% by weight.

Polyurethane polymer PP3 was prepared as follows:

590 g of Polyol Acclaim® 4200 N (polypropylene oxide diol, OH number 28.5 mg KOH/g; Bayer), 1180 g of Polyol Caradol® MD34-02 (polypropylene oxide-polyethylene oxide triol, OH number 35.0 mg KOH/g; Shell) and 230 g of isophorone diisocyanate (IPDI; Vestanat® IPDI, Degussa) were reacted by a known method at 80° C. to form an NCO-terminated polyurethane polymer. The reaction product had a free isocyanate group content, determined by titrimetry, of 2.12% by weight.

The urea thickener was prepared as follows:

A vacuum mixer was charged with 3000 g of diisodecyl phthalate (DIDP; Palatinol® Z, BASF) and 480 g of 4,4'-methylenediphenyl diisocyanate (MDI; Desmodur® 44 MC L, Bayer) and this initial charge was warmed slightly. Then 270 g of monobutylamine were added slowly dropwise with vigorous stirring. The resulting paste was stirred for a further hour under reduced pressure and with cooling.

Preparation of the Polyurethane Compositions:

In a vacuum mixer, 300 g of the above-described base composition PUR1 were processed together with the adjuvants listed in Table 4, in the absence of moisture, to give a lump-free, homogeneous paste, which was immediately filled into internally coated aluminum cartridges and given an airtight seal.

TABLE 4

Composition of Examples 27 to 31.

| Example | 300 g of base composition PUR1 and the following adjuvants: |
|---|---|
| 27 (Ref.)[a] | 3 g of tin cat.[b] |
| 28 | 3 g of tin cat.[b] and 3 g of aldiminoalkylsilane ALS2 |
| 29 | 3 g of tin cat.[b] and 3 g of aldiminoalkylsilane ALS3 |
| 30 (Ref.)[a] | 10.5 g of polyaldimine[c] and 0.3 g of acid cat.[d] |
| 31 | 10.5 g of polyaldimine[c], 0.3 g of acid cat.[d] and 3 g of aldiminoalkylsilane ALS2 |

[a]Reference examples without aldiminoalkylsilane
[b]Di-n-butyltin dichloride (1.8% by weight in DIDP)
[c]Dialdimine formed from 2,2-dimethyl-3-isobutyroxypropanal and 1,3-xylylenediamine
[d]Salicylic acid (5% by weight in dioctyl adipate)

The freshly prepared polyurethane compositions of Examples 27 to 31 were subsequently applied to a cleaned glass plate. The procedure adopted here was, for each of the examples, as follows:

A glass plate (float glass; Rocholl, Schönbrunn, Germany) measuring 10×15 cm was wiped on the air side (testing with UV light, wavelength 254 nm) three times each with a paper towel moistened with acetone. After a flash-off time of 5 minutes, the polyurethane composition was applied lengthwise to the glass plate from the cartridge, via a rounded tip, as beads of approximately 7 mm in diameter (15 cm bead length; 3 beads), the distance between two beads being at least 20 mm. Immediately following application, the beads were each covered lengthwise with an LDPE strip and, using a second glass plate, were compressed uniformly to a width of approximately 10 mm and a layer thickness of approximately 2 mm. The adhesive-coated glass plate was stored for 7 days under standard conditions (23±1° C., 50±5% relative humidity), in the course of which the polyurethane composition cured. Thereafter the first bead was tested for adhesion. The glass plate was then stored in water at room temperature for 7 days and left to dry, and the second bead was tested for adhesion. Subsequently the glass plate was stored for 7 days under hot, humid conditions (70° C., 100% humidity) and the third bead was tested for adhesion.

The test for adhesion was carried out as follows:

An incision was made into one end of the compressed bead of the cured polyurethane composition, just above the glass surface (bondline). The incised end of the bead was held with round-ended tweezers and then pulled by slow rolling up of the bead from the glass surface with a peeling action, in the direction of the other end of the bead. If, in the course of this removal, the adhesion was so strong that the end of the bead threatened to tear off when being pulled, a cutter was used to apply a cut perpendicular to the bead-pulling direction, down to the bare glass surface, and in this way a section of the bead was detached. Cuts of this kind were repeated, if necessary, on continued pulling, at a distance of 2 to 3 mm. In this way the entire bead was pulled and/or cut from the glass track. The adhesive properties were evaluated on the basis of the cured polyurethane composition which remained on the surface after the bead had been removed (cohesive fracture), this being accomplished by estimating the cohesive fraction of the bond area, in accordance with the following scale:

1=more than 95% cohesive fracture
2=75-95% cohesive fracture
3=25-75% cohesive fracture
4=less than 25% cohesive fracture
5=0% cohesive fracture (purely adhesive fracture)

Test results with cohesive fracture values of less than 75% are considered inadequate.

The results of the tests are set out in Table 5.

TABLE 5

Adhesion to glass of the polyurethane compositions of Examples 27 to 31.

| Example | Adhesion after storage under standard conditions | Adhesion after storage in water | Adhesion after storage under hot humid conditions |
|---|---|---|---|
| 27 (Ref.)[a] | 5 | 5 | 5 |
| 28 | 1 | 2 | 1 |
| 29 | 2 | 2 | 1 |
| 30 (Ref.)[a] | 5 | 5 | 5 |
| 31 | 1 | 1 | 1 |

[a]Reference examples without aldiminoalkylsilane

The results of Table 5 show that the Reference Examples 27 and 30 without aldiminoalkylsilanes exhibit no adhesion to glass, whereas Examples 28, 29 and 31 display good adhesion.

Examples 32 to 34

Examples 32 to 34 demonstrate the preparation of moisture-curing polyurethane compositions and their use as adhesives on aluminum.

Preparation of base composition PUR2:

In a vacuum mixer, 2100 g of polyurethane polymer PP4, 1500 g of calcined kaolin, 650 g of carbon black, 740 g of diisodecyl phthalate (DIDP; Palatinol® Z, BASF) and 10 g of p-tolylsulfonyl isocyanate (Zusatzmittel TI®, Bayer) were processed in the absence of moisture to give a lump-free, homogeneous paste, which was immediately filled into internally coated aluminum cartridges and given an airtight seal.

Polyurethane polymer PP4 was prepared as follows:

1125 g of Polyol Acclaim® 4200 N (polypropylene oxide diol, OH number 28.5 mg KOH/g; Bayer), 2250 g of Polyol Caradol® MD34-02 (polypropylene oxide-polyethylene oxide triol, OH number 35.0 mg KOH/g; Shell), 375 g of poly(hexamethylene carbonate) diol (OH number 130; Aldrich No. 46, 117-2), 750 g of 4,4'-methylenediphenyl diisocyanate (MDI; Desmodur® 44 MC L, Bayer) and 500 g of diisodecyl phthalate (DIDP; Palatinol® Z, BASF) were reacted by a known method at 80° C. to form an NCO-terminated polyurethane polymer. The reaction product had a free isocyanate group content, determined by titrimetry, of 2.55% by weight.

Preparation of the Polyurethane Compositions:

In a vacuum mixer, 300 g of the above-described base composition PUR2 were processed together with the adjuvants listed in Table 6, in the absence of moisture, to give a lump-free, homogeneous paste, which was immediately filled into internally coated aluminum cartridges and given an airtight seal.

TABLE 6

Composition of Examples 32 to 34.

| Example | 300 g of base composition PUR2 and the following adjuvants: |
|---|---|
| 32 (Ref.)[a] | 3 g of tin cat.[b] |
| 33 | 3 g of tin cat.[b] and 3 g of aldiminoalkylsilane ALS1 |
| 34 | 3 g of tin cat.[b] and 3 g of aldiminoalkylsilane ALS3 |

[a]Reference example without aldiminoalkylsilane
[b]Di-n-butyltin dichloride (1.8% by weight in DIDP)

The freshly prepared polyurethane compositions of Examples 32 to 34 were subsequently applied to cleaned aluminum plates. The procedure adopted here was, for each of the examples, as follows:

An untreated aluminum plate with low Si content (type AlMg3; Rocholl, Schönbrunn, Germany) or with high Si content (type AlMgSi1; Rocholl) measuring 30×20 cm was in each case abraded thoroughly on one side with abrasive wool and the abraded side was wiped three times each with a paper towel moistened with isopropanol. After a flash-off time of 5 minutes, the abraded side was pretreated with Sika® activator (available from Sika Schweiz AG) and then, after a further 15 minutes' flash-off time, the polyurethane composition was applied as beads of approximately 7 mm in diameter (15 cm bead length; 3 beads), the distance between two beads being at least 20 mm. Immediately following application, the beads were each covered lengthwise with an LDPE strip and, using a glass plate, were compressed uniformly to a width of approximately 10 mm and a layer thickness of approximately 2 mm. The aluminum plate was stored for 7 days under standard conditions (23±1° C., 50±5% relative humidity), in the course of which the polyurethane composition cured. Thereafter the first bead was tested for adhesion. The aluminum plate was then stored in water at room temperature for 7 days and left to dry, and the second bead was tested for adhesion. Subsequently the aluminum plate was stored for 7 days under hot, humid conditions (70° C., 100% humidity) and the third bead was tested for adhesion.

The test for adhesion and the evaluation of the adhesive properties were carried out as described for Examples 27 to 31.

The results of the tests are set out in Table 7.

TABLE 7

Adhesion to aluminum of the polyurethane compositions of Examples 32 to 34.

| Example | Adhesion after storage under standard conditions | | Adhesion after storage in water | | Adhesion after storage under hot humid conditions | |
|---|---|---|---|---|---|---|
| | AlMg3 | AlMgSi1 | AlMg3 | AlMgSi1 | AlMg3 | AlMgSi1 |
| 32 (Ref.)[a] | 4 | 4 | 3 | 2 | 3 | 1 |
| 33 | 1 | 1 | 2 | 2 | 1 | 1 |
| 34 | 1 | 1 | 2 | 1 | 1 | 1 |

[a]Reference example without aldiminoalkylsilane

The results of Table 7 show that Examples 33 and 34, with inventive aldiminoalkylsilanes, exhibit much better adhesion to aluminum than does the Reference Example 32 without aldiminoalkylsilane.

The invention claimed is:

1. An aldiminoalkylsilane ALS prepared from the reaction of at least one aminoalkylsilane AS of the formula (I)

and at least one aldehyde ALD of the formula (II),

the aldiminoalkylsilane ALS having the formula (VII) or (VIII)

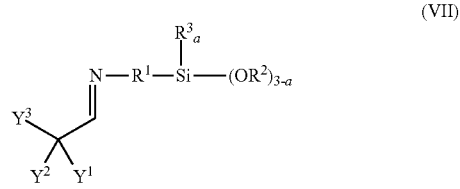

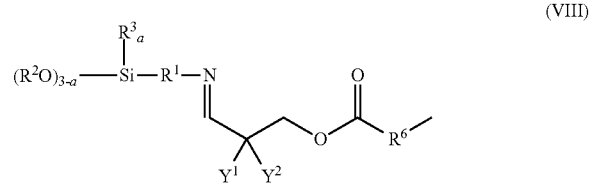

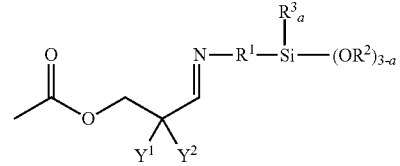

and wherein the aldehyde ALD of the formula (II) is further selected from aldehydes having the formula (III) or (IV)

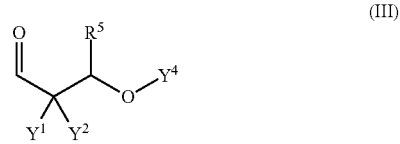

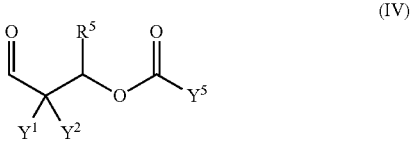

where
- $R^1$ is a linear or branched, optionally cyclic, alkylene group having 1 to 20 carbon atoms, optionally with aromatic components, and optionally with one or more heteroatoms;
- $R^2$ is an alkyl group having 1 to 5 carbon atoms;
- $R^3$ is an alkyl group having 1 to 8 carbon atoms;
- $a$ is 0, 1 or 2;
- $Y^1$ and $Y^2$ either are, independently of one another, each an organic radical; or together form a carbocyclic or heterocyclic ring which has a size of between 5 and 8 atoms;
- $R^6$ either is a linear or branched or cyclic alkylene chain having 2 to 16 carbon atoms, optionally having at least one heteroatom; or is a mono- or polyunsaturated, linear or branched or cyclic hydrocarbon chain having 2 to 16 carbon atoms; and
- $Y^3$ either is a substituted or unsubstituted alkyl group which has at least one heteroatom;
- $R^5$ is a hydrogen atom or is an alkyl or arylalkyl or aryl group;
- $Y^4$ is an alkyl or arylalkyl or aryl group; and
- $Y^5$ either is a hydrogen atom; or is an alkyl or arylalkyl or aryl group which optionally has at least one heteroatom, optionally contains at least one carboxyl group and optionally contains at least one ester group; or is a mono- or polyunsaturated, linear or branched hydrocarbon chain.

2. The aldiminoalkylsilane ALS of claim 1, wherein $R^1$ is a methylene, propylene, methylpropylene, butylene or dimethylbutylene group.

3. The aldiminoalkylsilane ALS of claim 1, wherein $R^2$ is a methyl group, an ethyl group or an isopropyl group.

4. The aldiminoalkylsilane ALS of claim 1, wherein $R^3$ is a methyl group or an ethyl group.

5. The aldiminoalkylsilane ALS of claim 1, wherein the aminoalkylsilane AS of the formula (I) is 3-aminopropyltrimethoxysilane, 3-aminopropyltriethoxysilane, 4-amino-3,3-dimethylbutyltrimethoxysilane, N-(2-aminoethyl)-3-aminopropyltrimethoxysilane or N-(2-aminoethyl)-3-aminopropyltriethoxysilane.

6. The aldiminoalkylsilane ALS of claim 1, wherein $R^5$ is a hydrogen atom; and
- $Y^5$ either is a linear or branched alkyl chain having 11 to 30 carbon atoms, optionally having at least one heteroatom; or is a mono- or polyunsaturated, linear or branched hydrocarbon chain having 11 to 30 carbon atoms; or is a radical of the formula (V) or (VI)

$$\cdots R^6 \underset{O}{\overset{O}{\|}} O \underset{Y^1 \ Y^2}{\overset{O}{\|}} \quad (V)$$

$$\cdots R^6 \underset{O}{\overset{O}{\|}} OR^7 \quad (VI)$$

where
- $R^6$ either is a linear or branched or cyclic alkylene chain having 2 to 16 carbon atoms, optionally having at least one heteroatom; or is a mono- or polyunsaturated, linear or branched or cyclic hydrocarbon chain having 2 to 16 carbon atoms; and
- $R^7$ is a linear or branched alkyl chain having 1 to 8 carbon atoms.

7. The aldiminoalkylsilane ALS of claim 1, wherein $Y^1=Y^2=$methyl.

8. The aldiminoalkylsilane ALS of claim 1, wherein the aldiminoalkylsilane ALS has the formula (VII')

$$\underset{Y^4}{\overset{R^5}{\underset{O}{\|}}} \underset{Y^2 \ Y^1}{\overset{N-R^1-Si-(OR^2)_{3-a}}{\|}} \quad (VII')$$

9. The aldiminoalkylsilane ALS of claim 1, wherein the aldehyde ALD used for preparing the aldiminoalkylsilane ALS is obtainable by an esterification reaction of a β-hydroxyaldehyde with a carboxylic acid, the β-hydroxyaldehyde being prepared, optionally in situ, from formaldehyde, and/or paraformaldehyde, and from a second aldehyde.

10. The aldiminoalkylsilane ALS of claim 9, wherein the aldehyde ALD used for preparing the aldiminoalkylsilane ALS is obtainable by an esterification reaction of 3-hydroxypivalaldehyde with a carboxylic acid, the 3-hydroxypivalaldehyde being prepared, optionally in situ, from formaldehyde, and/or paraformaldehyde, and from isobutyraldehyde.

11. The aldiminoalkylsilane ALS of claim 9, wherein the carboxylic acid used for preparing the aldehyde ALD is selected from the group consisting of lauric acid, myristic acid, palmitic acid, stearic acid, oleic acid, linoleic acid, linolenic acid, succinic acid, adipic acid, azelaic acid, sebacic acid, mixtures thereof and mixtures of fatty acids that comprise said acids.

12. A process for preparing an aldiminoalkylsilane ALS of claim 1, comprising reacting an aminoalkylsilane AS of the formula (I)

$$H_2N-R^1-\underset{}{\overset{R^3_a}{\underset{|}{Si}}}-(OR^2)_{3-a} \quad (I)$$

with at least one aldehyde ALD of the formula (II)

$$\underset{Y^1 \ Y^2}{\overset{O}{\|}}\underset{}{Y^3} \quad (II)$$

the water formed in the reaction being removed substantially or completely from the reaction mixture.

13. The process for preparing an aldiminoalkylsilane ALS of claim 12, wherein for preparing the aldiminoalkylsilane ALS the aldehyde groups of the aldehyde ALD are employed stoichiometrically or in a stoichiometric excess in relation to the primary amino groups of the aminoalkylsilane AS.

14. The process for preparing an aldiminoalkylsilane ALS of claim 12, wherein the aminoalkylsilane AS is present in a mixture of at least one polyamine having primary aliphatic amino groups and the aldehyde groups of the aldehyde ALD are employed stoichiometrically or in a stoichiometric excess relative to the entirety of the primary amino groups, thereby producing, after the reaction, a mixture comprising not only the aldiminoalkylsilane ALS but also the polyaldimine formed corresponding to the aldehyde ALD used.

15. A hydrolysis process comprising contacting an aldiminoalkylsilane ALS of claim 1 with water, wherein an aldehyde ALD of formula (II) is liberated.

16. A hydrolysis process comprising contacting an aldiminoalkylsilane ALS of claim 1 with water in the form of a water-containing component or water-releasing component, wherein an aldehyde ALD of formula (II) is liberated.

17. A moisture-curing polymer composition comprising at least one polymer containing isocyanate groups and/or silane groups, and
   at least one aldiminoalkylsilane ALS of claim 1.

18. The moisture-curing polymer composition of claim 17, wherein the polymer containing isocyanate groups and/or silane groups is a polyurethane polymer containing isocyanate groups and prepared from at least one polyisocyanate and at least one polyol, and the moisture-curing polymer composition is a moisture-curing polyurethane composition.

19. The moisture-curing polymer composition of claim 18, wherein the polyisocyanate for preparing the polyurethane polymer is a diisocyanate, selected from the group consisting of MDI, TDI, HDI, IPDI, and mixtures thereof.

20. The moisture-curing polymer composition of claim 18, wherein the polyol for preparing the polyurethane polymer has an average molecular weight of 1000 to 30 000 g/mol and an average OH functionality of 1.6 to 3.

21. The moisture-curing polymer composition of claim 17, wherein the aldiminoalkylsilane ALS is present in an amount of 0.01%-10% by weight in the polymer composition.

22. The moisture-curing polymer composition of claim 17, wherein in addition to the aldiminoalkylsilane ALS a polyaldimine is present.

23. The moisture-curing polymer composition of claim 22, wherein in the course of the hydrolysis of the polyaldimine an aldehyde ALD of the formula (II) is liberated.

24. A method of applying a moisture-curing polymer composition of claim 17, wherein said composition is contacted, during or after the application of the composition to a substrate, with atmospheric moisture or with water in the form of a water-containing component or water-releasing component, and subsequently cures, an aldehyde ALD of the formula (II) being liberated which remains substantially or completely in the cured polymer composition.

25. The method of claim 24, wherein the substrate is composed, at least in the region of application of the moisture-curing polymer composition, of glass, glass ceramic, concrete, natural stone, aluminum or automotive topcoat.

26. An adhesion promoter composition comprising at least one aldiminoalkylsilane ALS of claim 1, further comprising an aminoalkylsilane AS of the formula (I).

27. A method of applying an adhesion promoter composition of claim 26, wherein said composition is contacted, during or after the application to a substrate, with water or atmospheric moisture, before an adhesive, a sealant, a coating or a covering is applied thereto.

* * * * *